United States Patent
Nissum et al.

(10) Patent No.: US 8,871,527 B2
(45) Date of Patent: Oct. 28, 2014

(54) METHOD AND SYSTEM FOR MEASURING A SAMPLE TO DETERMINE THE PRESENCE OF AND OPTIONALLY TREAT A PATHOLOGIC CONDITION

(75) Inventors: Mikkel Nissum, Castellina in Chianti (IT); Christoph Eckerskorn, Ottobrunn (DE); Andreas Pfuetzner, Mainz (DE); Thomas Forst, Mainz (DE)

(73) Assignee: Becton, Dickinson and Company, Franklin Lakes, NJ (US)

(*) Notice: Subject to any disclaimer, the term of this patent is extended or adjusted under 35 U.S.C. 154(b) by 731 days.

(21) Appl. No.: 12/989,827

(22) PCT Filed: Apr. 29, 2009

(86) PCT No.: PCT/EP2009/055223
§ 371 (c)(1),
(2), (4) Date: Apr. 7, 2011

(87) PCT Pub. No.: WO2009/133152
PCT Pub. Date: Nov. 5, 2009

(65) Prior Publication Data
US 2011/0177537 A1    Jul. 21, 2011

Related U.S. Application Data

(60) Provisional application No. 61/048,704, filed on Apr. 29, 2008.

(51) Int. Cl.
*G01N 33/00* (2006.01)
*G01N 33/74* (2006.01)

(52) U.S. Cl.
CPC .......... *G01N 33/74* (2013.01); *G01N 2800/044* (2013.01); *G01N 2800/042* (2013.01); *Y10S 436/817* (2013.01)

USPC ............ 436/518; 436/514; 436/524; 436/817

(58) Field of Classification Search
None
See application file for complete search history.

(56) References Cited

U.S. PATENT DOCUMENTS

| | | | |
|---|---|---|---|
| 4,046,877 A | * | 9/1977 | White et al. ............... 514/15.2 |
| 5,447,612 A | | 9/1995 | Bier et al. |
| 5,500,374 A | | 3/1996 | Wenzhi |

(Continued)

FOREIGN PATENT DOCUMENTS

| | | | | |
|---|---|---|---|---|
| DE | 20 2006 009206 U1 | | 3/2007 | |
| DK | WO 2005/047508 | * | 5/2005 | ............. C07K 14/62 |

(Continued)

OTHER PUBLICATIONS

Owen (2004) Clin Chem 50: 257-259.*

(Continued)

*Primary Examiner* — Chris L Chin
*Assistant Examiner* — Richard Moerschell
(74) *Attorney, Agent, or Firm* — The Webb Law Firm

(57) ABSTRACT

The present invention provides diagnostic in vitro methods as well as kits and devices to be used in the methods of the present invention for diagnosis or prognosis of a pathologic condition characterized by the presence/absence of an endogenous hormone and/or hormone analog(s) thereof involved in diabetes or metabolic syndrome. The methods comprise a quantitative separation of at least those analytes of interest whose common presence interferes with measuring the presence/absence or concentration of one of the analytes of interest by a subsequent analytical method.

12 Claims, 9 Drawing Sheets

(56) References Cited

U.S. PATENT DOCUMENTS

| | | | |
|---|---|---|---|
| 6,328,868 B1 | 12/2001 | Weber | |
| 6,329,545 B1 * | 12/2001 | Larsen et al. | 562/439 |
| 6,416,643 B1 | 7/2002 | Henry et al. | |
| 6,541,263 B2 | 4/2003 | Gao | |
| 7,169,278 B2 | 1/2007 | Eckerskorn et al. | |
| 7,316,771 B2 | 1/2008 | Weber | |
| 2003/0153001 A1 * | 8/2003 | Soane et al. | 435/7.1 |
| 2006/0014670 A1 * | 1/2006 | Green et al. | 514/3 |
| 2006/0172436 A1 | 8/2006 | Hattori et al. | |
| 2006/0222698 A1 * | 10/2006 | Lau et al. | 424/450 |
| 2007/0065844 A1 * | 3/2007 | Golub et al. | 435/6 |
| 2008/0312256 A1 * | 12/2008 | Bebernitz et al. | 514/260.1 |
| 2009/0218224 A1 * | 9/2009 | Weber | 204/548 |

FOREIGN PATENT DOCUMENTS

| | | | |
|---|---|---|---|
| EP | 0 021 214 A1 | 1/1981 | |
| EP | 1 320 747 B1 | 3/2006 | |
| EP | WO 2007/147862 | * 12/2007 | G01N 27/447 |
| WO | 02/50524 A2 | 6/2002 | |
| WO | 2007/147862 A1 | 12/2007 | |
| WO | 2008/025806 A1 | 3/2008 | |
| WO | 2008/053047 | 5/2008 | |
| WO | 2008/087218 | 7/2008 | |

OTHER PUBLICATIONS

Pace (1992) Biochemistry 31: 725-732.*

Hunter (2003) Diabetes 52: 492-498.*

Hunter et al., "Demonstration of Glycated Insulin in Human Diabetic Plasma and Decreased Biological Activity Assessed by Euglycemic-Hyperinsulinemic Clamp Technique in Humans", Diabetes, vol. 52, No. 2, Feb. 2003, pp. 492-498.

Guillo et al., "Two-color electrophoretic immunoassay for simultaneous measurement of insulin and glucagon content in islets of Langerhans", Electrophoresis, vol. 29, No. 2, Dec. 2007, pp. 410-416.

* cited by examiner

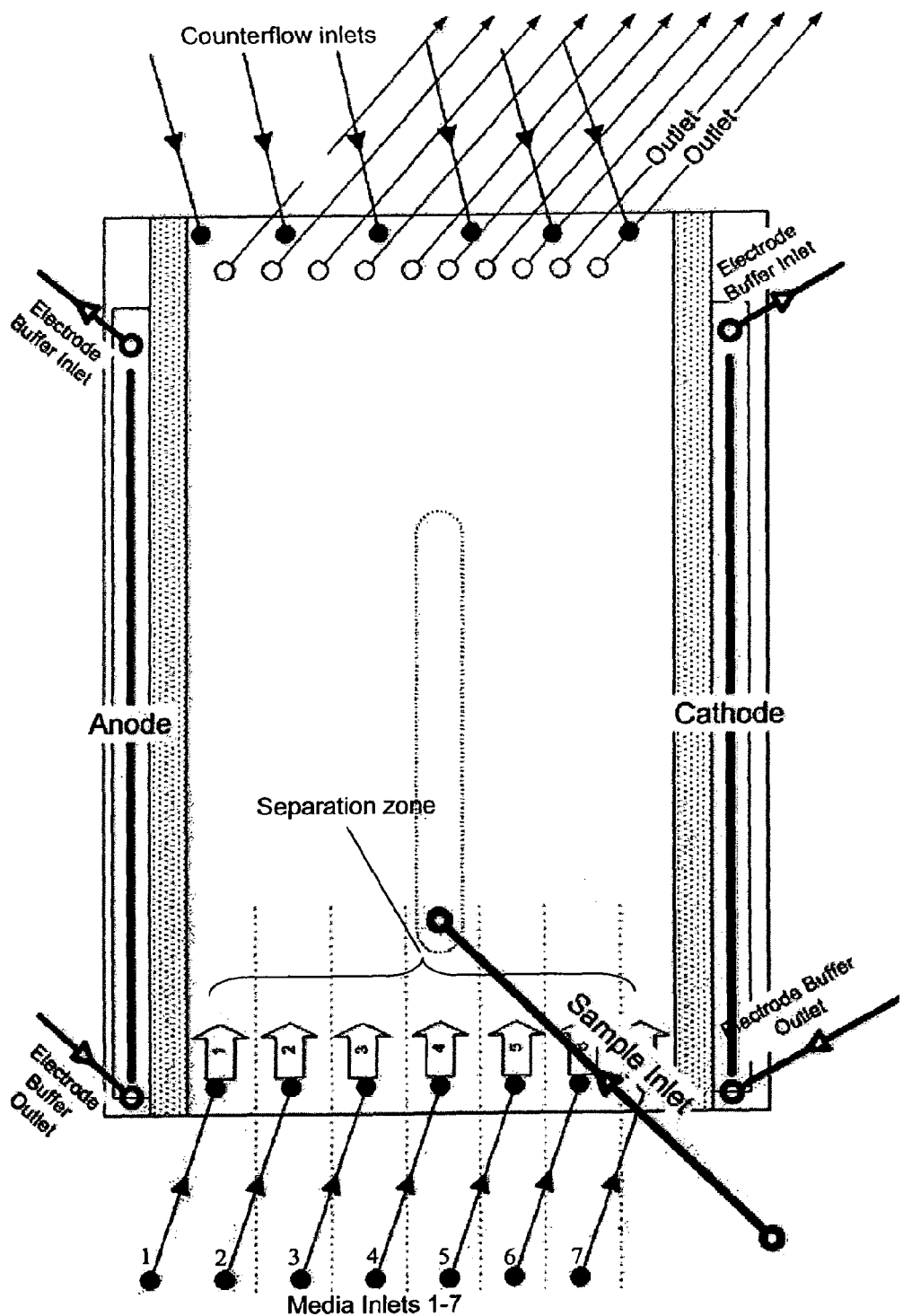
Fig. 1: Schematic view of an FFE Apparatus

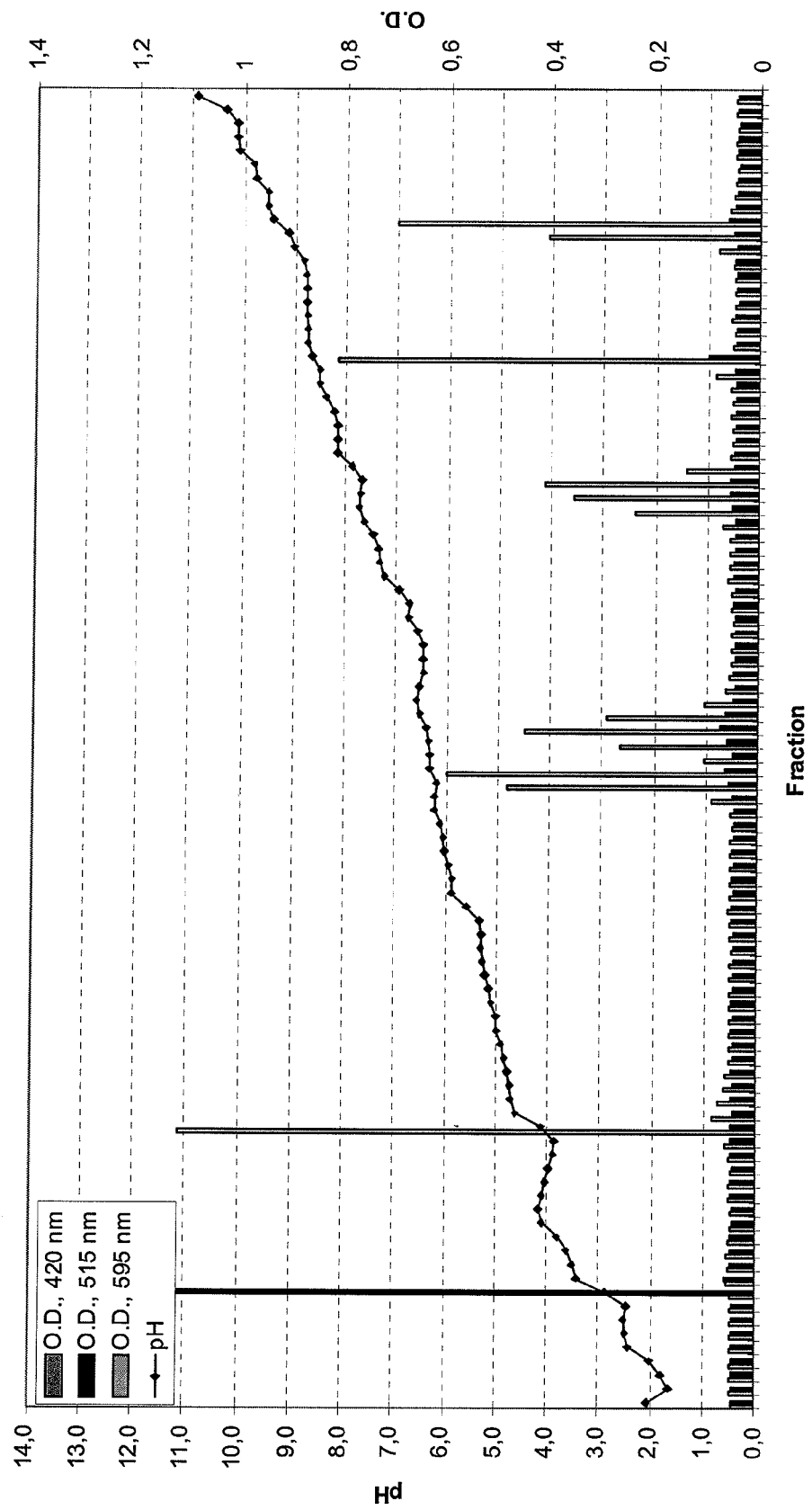
Fig. 2: Elution profile of pI markers of an insulin Detemir standard

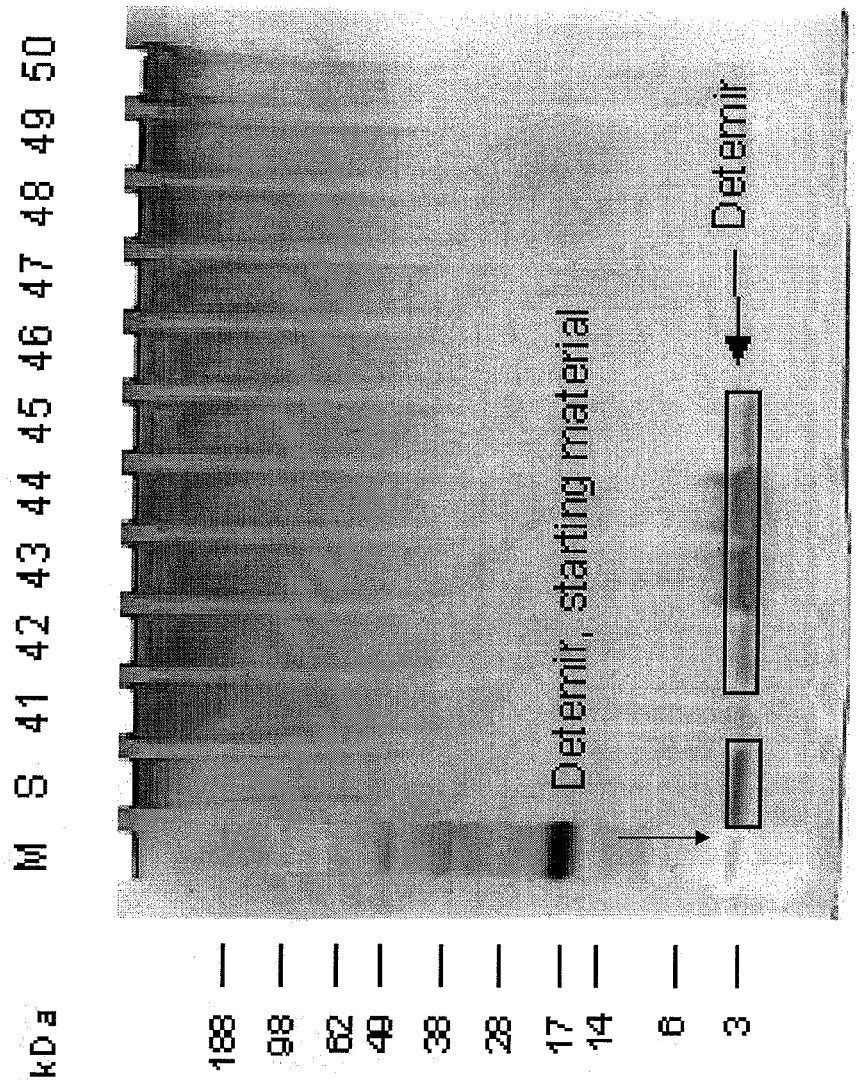

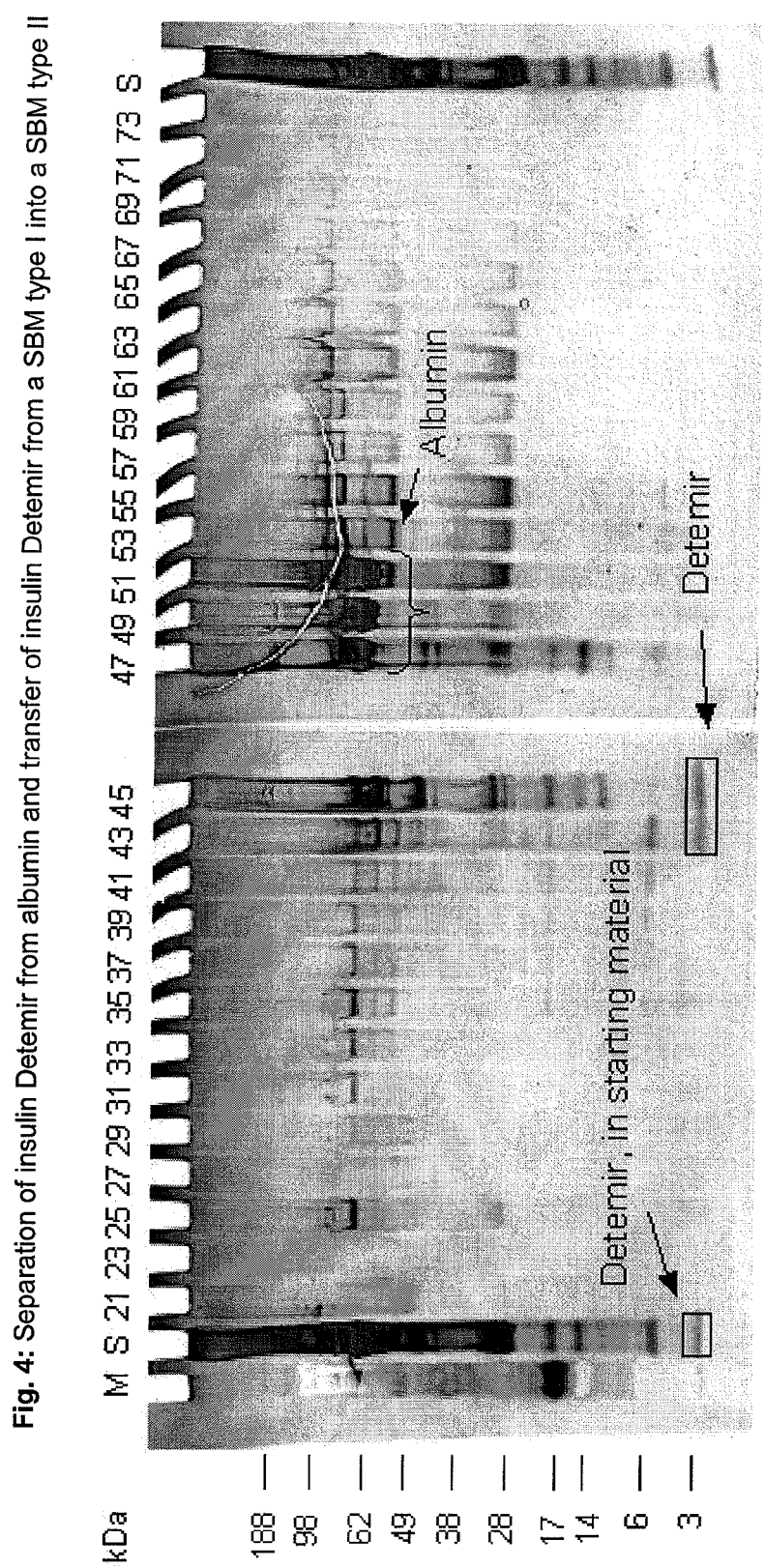
Fig. 4: Separation of insulin Detemir from albumin and transfer of insulin Detemir from a SBM type I into a SBM type II

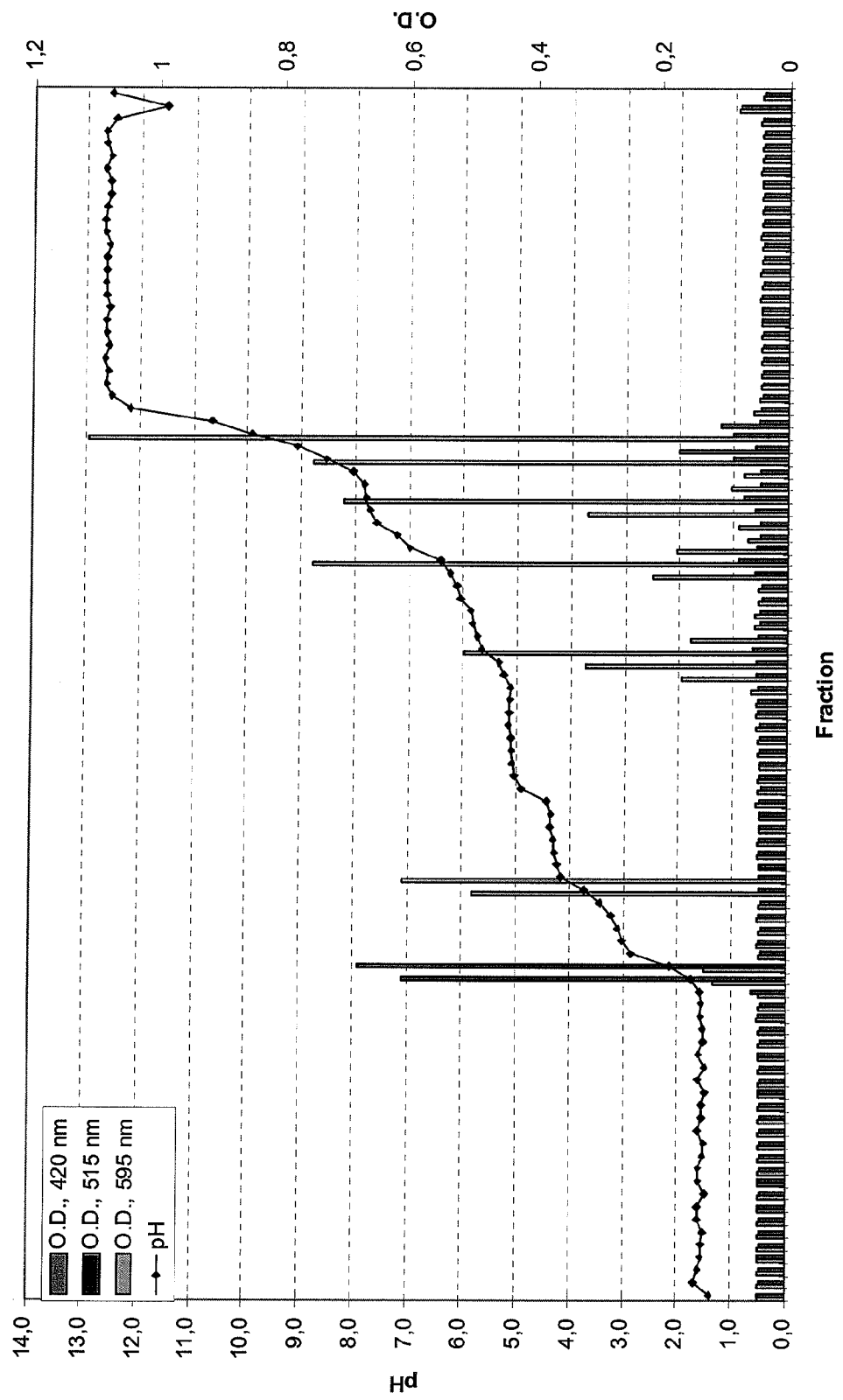
Fig. 5: Elution profile of pI markers of a human serum sample

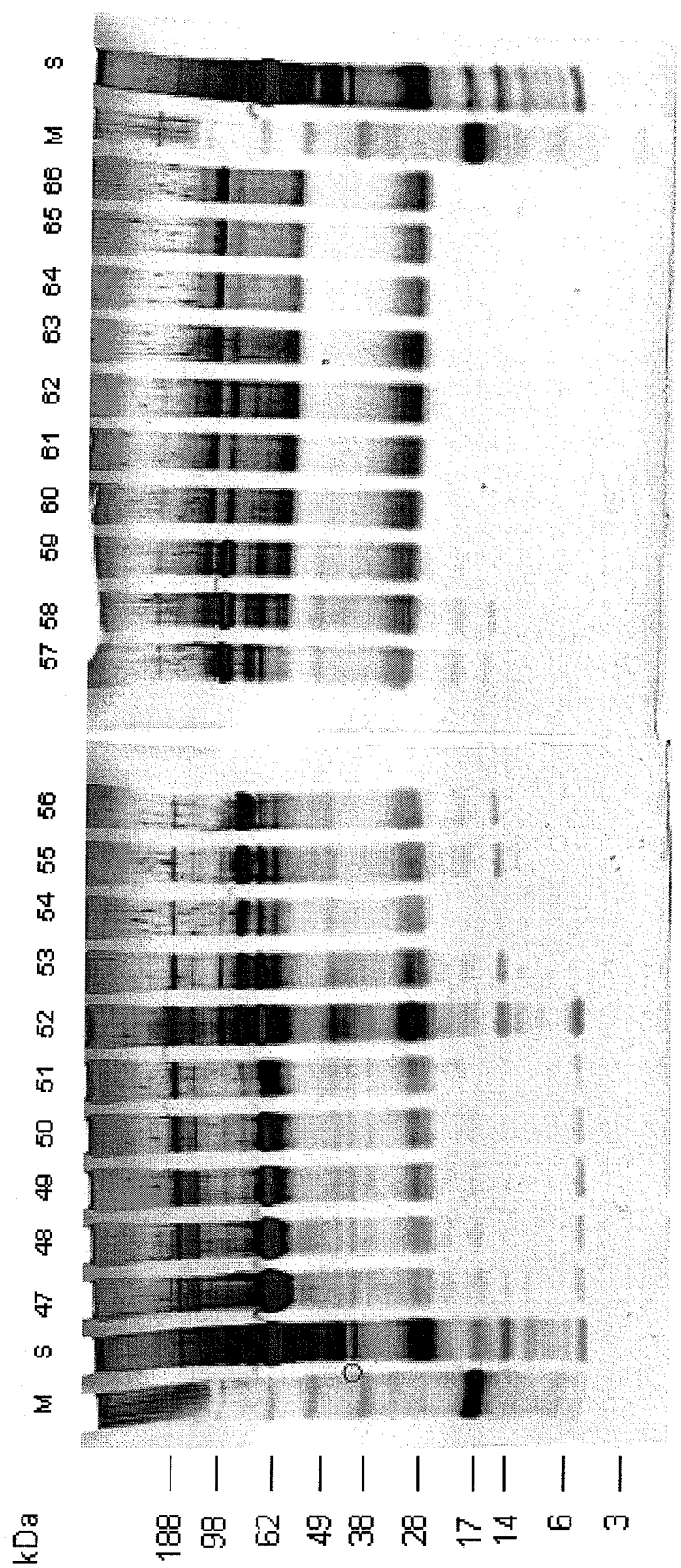
Fig. 6: Human serum sample without insulin or analogs thereof

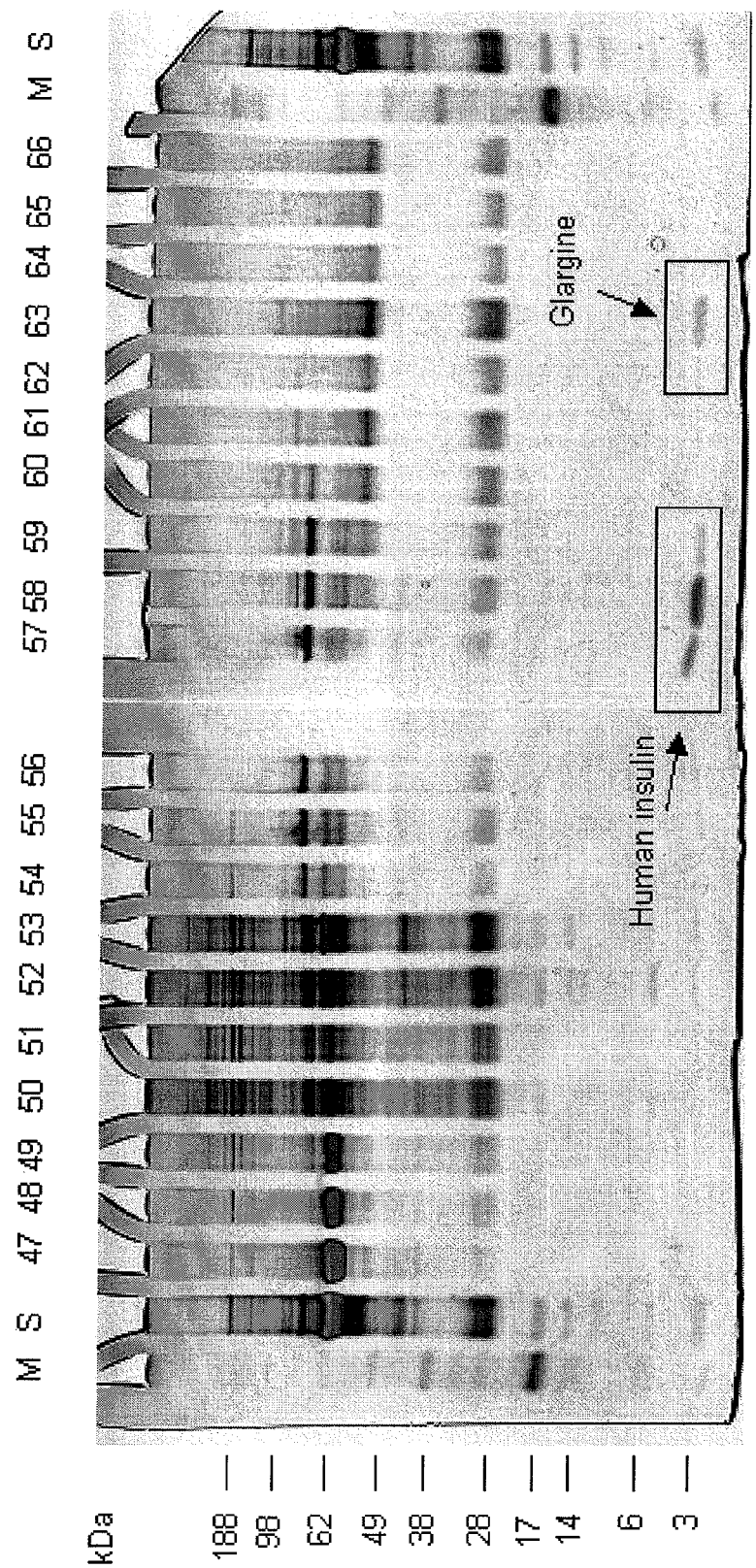
Fig. 7: Separation of Glargine and human insulin

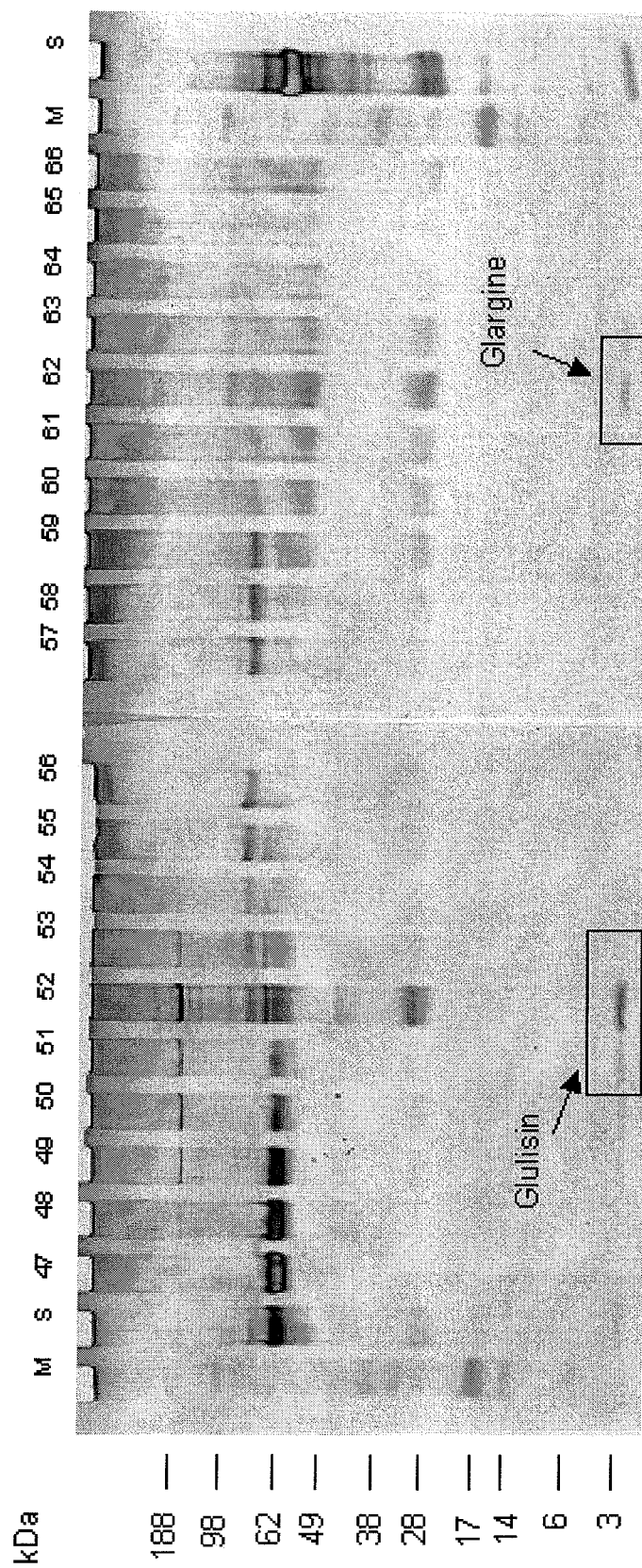
Fig. 8: Separation of Glargine and Glulisine

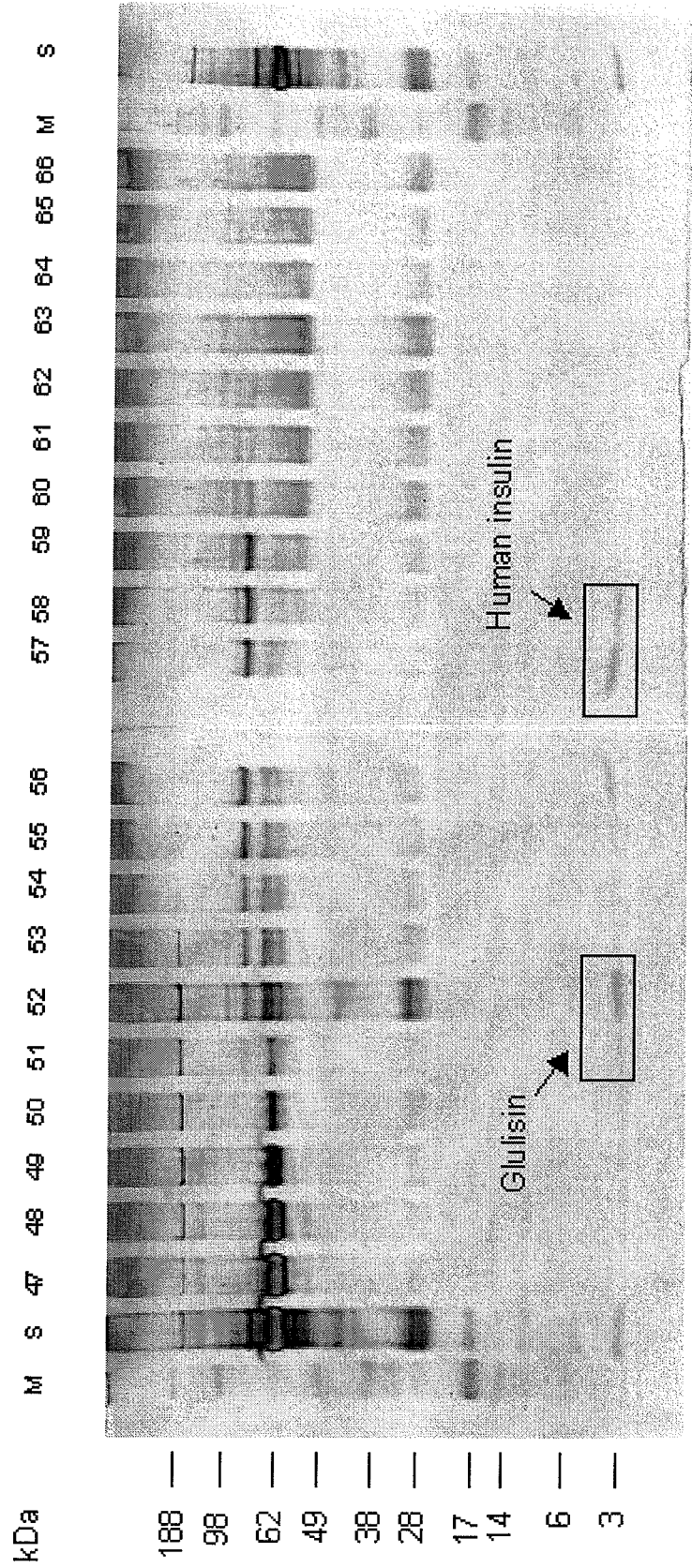
Fig 9: Separation of Glulisine and human insulin

```
SEQUENCE LISTING

<160> NUMBER OF SEQ ID NOS: 12

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: glargine alpha chain

<400> SEQUENCE: 3

Gly Ile Val Glu Gln Cys Cys Thr Ser Ile Cys Ser Leu Tyr Gln Leu
1               5                   10                  15

Glu Asn Cys Tyr Gly
            20
```

```
<210> SEQ ID NO 4
<211> LENGTH: 32
<212> TYPE: PRT
<213> ORGANISM: Artificial Sequence
<220> FEATURE:
<223> OTHER INFORMATION: glargine beta chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 5
<211> LENGTH: 21
<212> TYPE: PRT
<213> ORGANISM: Artificial Sequence
<220> FEATURE:
<223> OTHER INFORMATION: lispro alpha chain

<400> SEQUENCE: 5

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 6
<211> LENGTH: 30
<212> TYPE: PRT
<213> ORGANISM: Artificial Sequence
<220> FEATURE:
<223> OTHER INFORMATION: lispro beta chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 7
<211> LENGTH: 21
<212> TYPE: PRT
<213> ORGANISM: Artificial Sequence
<220> FEATURE:
<223> OTHER INFORMATION: aspart alpha chain

<400> SEQUENCE: 7

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 8
<211> LENGTH: 30
<212> TYPE: PRT
<213> ORGANISM: Artificial Sequence
<220> FEATURE:
<223> OTHER INFORMATION: aspart beta chain

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

```
<210> SEQ ID NO 9
<211> LENGTH: 21
<212> TYPE: PRT
<213> ORGANISM: Artificial Sequence
<220> FEATURE:
<223> OTHER INFORMATION: glulisine alpha chain

<400> SEQUENCE: 9

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 10
<211> LENGTH: 30
<212> TYPE: PRT
<213> ORGANISM: Artificial Sequence
<220> FEATURE:
<223> OTHER INFORMATION: glulisine beta chain

<400> SEQUENCE: 10

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 11
<211> LENGTH: 21
<212> TYPE: PRT
<213> ORGANISM: Artificial Sequence
<220> FEATURE:
<223> OTHER INFORMATION: detemir alpha chain

<400> SEQUENCE: 11

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 12
<211> LENGTH: 29
<212> TYPE: PRT
<213> ORGANISM: Artificial Sequence
<220> FEATURE:
<223> OTHER INFORMATION: detemir beta chain
<220> FEATURE:
<221> NAME/KEY: MOD_RES
<222> LOCATION: (29)..(29)
<223> OTHER INFORMATION: ACETYLATION

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

METHOD AND SYSTEM FOR MEASURING A SAMPLE TO DETERMINE THE PRESENCE OF AND OPTIONALLY TREAT A PATHOLOGIC CONDITION

The Sequence Listing associated with this application is filed in electronic format via EFS-Web and is hereby incorporated by reference into the specification in its entirety. The name of the text file containing the Sequence Listing is 103375_ST25.txt. The size of the text file is 4,462 bytes, and the text file was created on Jul. 22, 2014.

FIELD OF THE INVENTION

Aspects of the invention generally relate to the diagnosis, prognosis, and treatment of diseases or conditions.

BACKGROUND OF THE INVENTION

The determination of the presence of analogs/isoforms of endogenous compounds is a growing field in clinical and research medical science. Such diagnostic methods are useful in, e.g., the treatment of diabetes, the treatment of metabolic syndrome, or doping controls.

Current methods for assessing the risk for or diagnosing pathologic conditions such as diabetes often rely on a diagnosis by attrition, a process of elimination or by invasive surgery or biopsies. In certain diseases, such as metabolic disease or doping, the methods by which an objective diagnosis may be made are often indirect, cumbersome, time-consuming and costly, see, e.g., LC-MS/MS.

During the past decade, several therapeutic peptides and proteins have been developed for the treatment of patients with diabetes mellitus and metabolic syndrome. After the introduction of recombinant human insulin in the 1980ies, insulin analogs have been approved for treatment that vary in their amino acid sequence, and in consequence have a different pharmacokinetic profile. Next to short acting insulin analogs (insulin Lispro (Eli Lilly & Co, Indianapolis, Ind.), insulin Aspart (Novo Nordisk Pharmaceuticals, Baulkham Hills, Australia), and insulin Glulisine (Aventis, Bridgewater, NL)) for prandial insulin substitution, longer acting basal insulin analogs (insulin Glargine (Sanofis-Aventis, Frankfurt am Main, Del.) and insulin Detemir (Novo Nordisk Pharmaceuticals, Baulkham Hills, AU) provide the insulin coverage for the remaining portions of the day not covered by short-acting insulin analogs. As combinations of these analogs provide several clinical advantages towards regular human insulin (e.g. less risk of hypoglycemia or no requirement of an injection to meal interval), they are nowadays widespreadly used worldwide. In some clinical situations (e.g. hypoglycemia) and also in many scientific projects, it has become desirable to be able to specifically measure the concentrations of these analogs in the blood of patients and thus multiple efforts have been undertaken to develop analog-specific immunoassays for these determinations. However, as of today only one assay that is specific for insulin Lispro is commercially available after many years of developmental efforts (Millipore, St. Charles, US).

Indirect assessments are only possible by means of cross-reactive insulin assays, which, however, cannot distinguish between regular human insulin and/or several analogs thereof.

For example, Owen and Roberts (2004) describe cross-reactivity of three recombinant insulin analogs with five commercial insulin immunoassays.

Lindström et al. (2002) disclose a double-antibody technique to describe the pharmacokinetics of the rapid-acting insulin analogs Aspart and Lispro. The antibody used recognizes human insulin but does not cross-react or specifically distinguish the two insulin analogs. The combination of such an immuno assay with a second immuno assay using an antibody that cross-reacts with all three forms allows a determination of the ratio between insulin and its two analogs, but these tests do not allow a differentiation between the two analogs or the determination of other basal and rapid-acting insulin analogs and insulin.

Bowsher et al. (1999) describes a radio immuno assay (RIA) for the specific determination of insulin Lispro that does not show interference from insulin, proinsuline, or C-peptide and has interassay CVs of 2.6-13.4%. However, the antiserum does not allow a differentiation between further analogs of insulin and insulin.

Andersen et al. (2000) describe an insulin immunoassay specific for the rapid-acting insulin analog insulin Aspartat. Nevertheless, the assay does not distinguish further analogs of insulin and is not commercially available.

Cao et al. (2001) describe an immunoassay for the determination of carboxyl-terminal B-chain analogues of human insulin that can quantify human insulin, proinsuline, despentapeptide insulin, procine insulin and insulin Lispro with comparable cross-reactivity, i.e. it shows cross-reactions between the listed analogs and is predicted to show cross reaction to further analogs.

An Elecsys® assay of free insulin determination and the absence of cross-reactivity with insulin Lispro is disclosed in Sapin et al. (Clin. Chim. Acta 2001). However, the assay cross-reacts with further insulin analogs such as pig insulin.

Up to date, the common presence or concentration of further human insulin analogs and endogenous human insulin in a patient's sample (for example, a blood sample) can only be determined in the common presence of the insulin forms by means of sophisticated and work-intense analytical methods with unreasonable requirements as regards costs and human resources (e.g. liquid chromatography-tandem mass spectrometry (LC-MS/MS)).

Thevis et al. (2005) describe a qualitative determination of synthetic analogs of insulin in human plasma by immuno affinity purification and liquid chromatography-tandem mass spectrometry (LC-MS/MS) for doping control purposes. However, this method requires extensive sample preparation prior and subsequent to the chromatographic step.

Cao et al. (2006) report of HPLC-MS method development for quantification of insulin and its analogs and for identification of the source of discrepancy among immunoassay methods. Similar to the method described in Thevis et al., the HPLC-MS method requires extensive sample preparation.

Electrophoresis is a well-established technology for separating particles based on the migration of charged particles under the influence of a direct electric current. Several different operation modes such as isoelectric focusing (IEF), zone electrophoresis (ZE) and isotachophoresis (ITP) have been developed as variants of the above separation principle and are generally known to those of skill in the art.

IEF (isoelectric focusing), one of the above general operation modes of electrophoresis, including free flow electrophoresis, is a technique commonly employed, e.g., in protein characterization as a mechanism to determine a protein's isoelectric point (see, e.g., Analytical Biochemistry, Addison Wesley Longman Limited-Third Edition, 1998) or to separate analytes according to their isoelectric point (pI). IEF is discussed in various texts such as Isoelectric Focusing by P. G. Righetti and J. W. Drysdale (North Holland Publ., Amsterdam, and American Elsevier Publ., New York, 1976). Zone electrophoresis (ZE) is another alternative operation mode based on the difference between the electrophoretic mobility value of the particles to be separated and the charged species of the separation medium employed.

WO 2007/147862, which is herewith incorporated in its entirety, discloses combinations of ZE and IEF in FFE.

Isotachophoresis (ITP) is a more recent variant of electrophoresis wherein the separation is carried out in a discontinuous buffer system. Sample material to be separated is inserted between a "leading electrolyte" and a "terminating electrolyte", the characteristics of buffers being that the leader will comprise ions having a net electrophoretic mobility higher than those of the sample ions, while the terminator must comprise ions having a net electrophoretic mobility lower than those of the sample ions. In such a system, sample components sort themselves from leader to terminator in accordance with their decreasing mobilities in a complex pattern governed by the so-called Kohlrausch regulating function. The process has been described in the art, for instance, in Bier and Allgyer, Electrokinetic Separation Methods 443-69 (Elsevier/North-Holland 1979).

International patent application PCT/EP2007/061840, which is incorporated herein by reference in its entirety, refers to media combinations for enhanced free flow ITP.

Among electrophoretic technologies, free flow electrophoresis (FFE) is one of the most promising [Krivanova L. & Bocek P. (1998), "Continuous free-flow electrophoresis", Electrophoresis 19: 1064-1074]. FFE is a technology wherein the separation of the analytes occurs in a carrier-free medium, i.e., a liquid (aqueous) medium in the absence of a stationary phase (or solid support material) to minimize sample loss by adsorption. FFE is often referred to as carrier-less deflection electrophoresis or matrix-free deflection electrophoresis.

A particular FFE technique referred to as interval FFE is disclosed, for example, in U.S. Pat. No. 6,328,868. In this patent, the sample and separation medium are both introduced into an electrophoresis chamber, and the analytes in the sample are separated using an electrophoresis mode such as ZE, IEF or ITP, and are finally expelled from the chamber through fractionation outlets. Embodiments of the '868 patent describe the separation media and sample movement to be unidirectional, traveling from the inlet end towards the outlet end of the chamber, with an effective voltage applied causing electrophoretic migration to occur while the sample and media are not being fluidically driven from the inlet end towards the outlet end, in contrast to the technique commonly used in the art wherein the sample and media pass through the apparatus while being separated in an electrical field (commonly referred to as continuous FFE).

Another particular FFE technique referred to as cyclic or cyclic interval mode has been described in International application WO 2008/025806, hereby incorporated by reference in its entirety. In sum, the cyclic interval mode is characterized by at least one, and possible multiple reversals of the bulk flow direction while the sample is being held in the electrophoretic field between the elongated electrodes. In contrast to static interval mode, the sample is constantly in motion thereby allowing higher field strength and thus better (or faster) separation. Additionally, by reversing the bulk flow of the sample between the elongated electrodes, the residence time of the analytes in the electrical field can be increased considerably, thereby offering increased separation time and/or higher separation efficiency and better resolution. The reversal of the bulk flow into either direction parallel to the elongated electrodes (termed a cycle) can be repeated for as often as needed in the specific situation, although practical reasons and the desire to obtain a separation in a short time will typically limit the number of cycles carried out in this mode.

International patent application WO 2002/50524 A and U.S. patent application 2004/050698 and International patent application PCT/EP2007/061840, which are incorporated herein by reference in their entireties, disclose an FFE apparatus useful for FFE separations as described above.

A number of separation media for the separation of analytes such as bioparticles and biopolymers are known in the art. For example, the book "Free-flow Electrophoresis", published by K. Hannig and K. H. Heidrich, (ISBN 3-921956-88-9) reports a list of separation media suitable for FFE and in particular for free flow ZE (FF-ZE).

U.S. Pat. No. 5,447,612 discloses another separation medium which is a pH buffering system for separating analytes by isoelectric focusing by forming functionally stable pre-cast narrow pH zone gradients in free solution. It employs buffering components in complementary buffer pairs.

Binary buffer systems referred to herein as "NB buffer systems" are disclosed in detail in International patent application PCT/EP2008/050597, which is incorporated herein by reference in its entirety. The buffer system comprises at least one buffer acid and at least one buffer base, with the proviso that the pKa value of the buffer acid must be higher than the pH of the separation buffer medium (SBM) and the pKa of the buffer base is lower than the pH of the SBM. Put another way, the pKa of the buffer acid will be higher than the pKa of the buffer base.

U.S. co-pending provisional applications U.S. Ser. Nos. 60/945,246 and 60/987,208, which are incorporated herein by reference in their entireties, refer to volatile buffer systems suitable for FFE. The volatile buffer systems offer the advantage that they can be easily removed subsequent to a FFE step and prior to a downstream analysis such as MS, or that they do not disturb a downstream analysis.

SUMMARY OF THE INVENTION

The availability of a pre-analytical method that allows for specific separation of modified peptide hormones (e.g., endogenous hormones and analog(s) thereof) and thus enables their identification and quantification even by techniques such as cross-reactive immunoassays would provide a tremendous developmental and clinical support and would represent an economical solution to these analytical laboratory problems.

Such a pre-analytical separation would address the constant need in medicine for less invasive, less physically taxing, and more accurate ways to diagnose and treat diseases/pathological conditions.

The present invention provides diagnostic methods as well as kits and devices to be used in the methods of embodiments of the present invention.

Thus, a first aspect of the present invention relates to an method useful for diagnosis or prognosis of a pathologic condition characterized by the presence/absence of an endogenous hormone and/or hormone analog(s) thereof involved in diabetes or metabolic syndrome (analytes of interest) comprising:

(a) quantitative separation of at least one of the hormone analog(s) and the endogenous hormone, or quantitative separation of at least two of the hormone analogs from a sample into a multiplicity of fractions and collection of at least those fractions comprising an endogenous hormone and/or hormone analog(s) thereof;

with the proviso that if the common presence of the analog(s) and/or the endogenous hormone in the same fraction(s) interferes with measuring a parameter of one of said hormone analog(s) and/or said endogenous hormone by an analytical method employed in step (b), at least such hormone analog(s) and/or the endogenous hormone must be separated from each other in step (a);

(b) measuring at least one parameter of the endogenous hormone or analog(s) thereof in one or more fraction(s) that comprises the hormone and/or analog(s) of interest by an analytical method.

A second aspect relates to a method useful for diagnosis or prognosis of a pathologic condition characterized by the presence/absence of an endogenous hormone and/or hormone analog(s) thereof involved in diabetes or metabolic syndrome comprising:

(a) quantitative separation of at least one of the hormone analog(s) and the endogenous hormone, or quantitative separation of at least two of the hormone analogs from a sample into a multiplicity of fractions;
with the proviso that if the common presence of the analog(s) and/or the endogenous hormone in the same fraction(s) interferes with measuring a parameter of one of said hormone analog(s) and/or said endogenous hormone by an analytical method employed in step (b), at least such hormone analog(s) and/or the endogenous hormone must be separated from each other in step (a);

(b) online measuring at least one parameter of the endogenous hormone or analog(s) thereof in one or more fraction(s) that comprises the hormone and/or analog(s) of interest by an analytical method not involving mass spectrometry.

A third aspect of the present invention relates to a method for determining the absence/presence of at least one hormone form of an endogenous hormone that is involved in diabetes or metabolic syndrome comprising:

(a) a liquid phase matrix free electrophoretic method for separating hormone form(s) whose common presence with the hormone form of interest in the same fraction(s) interfere with measuring a parameter of the hormone form of interest by an analytical method employed in step (b); and (b) measuring at least one parameter of the hormone form of interest in one or more fraction(s) that are predicted to comprise the hormone form of interest by an analytical method.

A fourth aspect of the present invention relates to a kit to perform a method according to the present invention comprising a standard of an endogenous hormone and/or analogs thereof according to the present invention and buffer components for the preparation of at least one separation buffer medium to perform a separation step (step (a)) and, alternatively, components to prepare the analytical buffer(s) to perform a subsequent analytical step (step (b)).

A fifth aspect relates to an FFE apparatus for carrying out a FFE separation comprised in a method according to embodiments of the present invention comprising:

an electrophoresis chamber comprising a set of electrodes, wherein at least one of the electrodes is a cathode and at least one of the electrodes is an anode, and a separation zone interposed therebetween, wherein the apparatus further contains means for introducing SBM's into the separation zone; and optionally, means for forming stabilizing media within the separation zone; and fraction outlets that transfer the fractions into a suitable container to perform a subsequent analytical method according to step (b), or, optionally, fraction outlets that are combined with a subsequent online analytical device.

BRIEF DESCRIPTION OF FIGURES

FIG. 1 shows a schematic view of a free flow electrophoresis apparatus.

FIG. 2 shows the fractional separation of an insulin Detemir standard between anode (left) and cathode (right) (96 fractions) and indicates the pH of the fractions Colored pI-markers were separated to evaluate the separation performance of the system. The absorbance of each fraction at $\lambda=420$ nm, 515 nm and 595 nm which represent the absorbance of the respective pI-markers are also reported in FIG. 2.

FIG. 3 shows the corresponding silver stained SDS-PAGE gel obtained for the various fractions of the FFE separation. The gel demonstrates the elution profile of insulin Detemir.

FIG. 4 shows the corresponding silver stained SDS-PAGE gel obtained for the various fractions of a sample comprising insulin Detemir that was spiked into a human blood plasma sample. The sample was introduced into a zone yielding denaturing conditions and separated by FFE. Insulin Detemir was separated from albumin and transferred into a zone yielding non-denaturing conditions. The gel demonstrates the essential depletion of albumin from fractions comprising insulin Detemir.

FIG. 5 shows the fractional separation of a human serum sample between anode (left) and cathode (right) (96 fractions) by FFE and indicates the pH of the fractions. Colored pI-markers were separated to evaluate the separation performance of the system. The absorbance of each fraction at $\lambda=420$ nm, 515 nm and 595 nm which represent the absorbance of the respective pI-markers are also reported in FIG. 5.

FIG. 6 shows the corresponding silver stained SDS-PAGE gel obtained for the various fractions demonstrating the elution profile of the sample without insulin or analog(s) thereof.

FIG. 7 shows the silver stained SDS-PAGE gel obtained for the various fractions of the FFE separation of insulin Glargine and human insulin that were spiked in a human serum sample demonstrating the quantitative separation of insulin Glargine from human insulin.

FIG. 8 shows the silver stained SDS-PAGE gel obtained for the various fractions of the FFE separation of insulin Glargine and insulin Glulisine that were spiked in a human serum sample demonstrating the quantitative separation of insulin Glargine from insulin Glulisine.

FIG. 9 shows the silver stained SDS-PAGE gel obtained for the various fractions of the FFE separation of human insulin and insulin Glulisine that were spiked in a human serum sample demonstrating the quantitative separation of human insulin from insulin Glulisine.

DETAILED DESCRIPTION

The satisfactory analysis of mixtures of endogenous hormones and/or analogs thereof has been often hampered by the cross-reactivity of commercially available immuno assays, i.e., the immuno assays do not allow the simultaneous determination of a composition of, e.g., different insulin forms.

There have been attempts in the art to overcome these problems by developing improved, highly specific antibodies showing less or no cross-reactivity to non-targeted isoforms. However these attempts have only been successful in isolated circumstances.

Alternatively, those of skill in the art have tried to move away from immuno assays and rather employ highly sophisticated analytic methods including mass spectrometry (MS), e.g., LC-MS/MS. However, these methods require extensive sample preparation and are not capable of quantitatively separating the hormone forms in collectable fractions thereby inter alia permitting the ability to retain the samples' native conditions. Rather, the MS application itself is used to differentiate the hormone forms that are present in a sample.

In contrast to these attempts directed at improving the accuracy and specificity of these analytical methods, embodiments of the present invention aim at providing methods and kits that offer an enhanced separation of analytes of interest whose common presence in a sample would otherwise interfere with the measurement of a parameter of one of the analytes of interest by a subsequent analytical method. In contrast to methods known in the art, the methods yielding an enhanced resolution do not only allow the use of otherwise cross-reactive analytical methods to analyze and quantify mixtures of endogenous hormones and/or analogs thereof, but further improve the sensitivity of subsequent analytical methods, for example by reducing the background in a sample.

In other words, the quantitative separation of analytes of interest from each other and, optionally from further compounds during the separation step makes it possible to use even cross-reactive analytical methods such as cross-reactive immuno assays and further analytical methods, such as Raman-spectroscopy or SPR for the detection/analysis/measurement of separated analytes of interest.

The provision of effective separation techniques that do not require the extensive sample preparation required for sophisticated and expensive analytical methods such as MS provides many advantages. Apart from reducing the biological background of a sample by fractionating the sample into a multiplicity of fractions, the methods of the present invention further offer the advantage of multiplexing a sample, i.e., allowing the detection of more than one different endogenous compound and/or analogs of the endogenous compounds in one sample.

Aspects of the present invention relate to new in vitro methods comprising a pre-analytic separation of analytes of interest and a subsequent analysis of the separated analytes of interest as a means to, e.g., diagnose or prognosticate a pathologic condition such as diabetes and metabolic syndrome. For example, after the optional identification (if not known) of the free flow electrophoretic (FFE) characteristics of endogenous insulin and/or analog(s) thereof present in a sample, the FFE fractions containing the quantitatively separated analytes, i.e., the endogenous insulin and/or analog(s) thereof, can be subjected without the need of a buffer exchange step to an ELISA for regular human insulin (Invitron, Cardiff, UK) which is cross-reactive to all insulin analogs. Further examples are found in the emerging area of hormones involved in appetite regulation, e.g. the newly developed anti-diabetic drug class of the glucagon-like-peptide 1 (GLP-1) derived analogs (e.g., exenatide and/or liraglutide) or analogs of e.g. ghrelin, cholecystokinin (CKK), or obestatin that will at some point enter the clinical development phase and create further analytical demands that cannot be addressed by the currently available assay methods.

The term "a" as used herein means one, at least one or one or more.

The term "multiplexing" in the context of the present invention refers to the simultaneous measurement of several different endogenous compounds by measuring at least one parameter that individually correlates with the presence/absence of one of the different endogenous compounds. Accordingly, a multiplexed assay allows simultaneous measurement of several different endogenous compounds comprised in a sample. This principle also encompasses analogs of the different endogenous compounds. As a non-limiting example, a method according to the present invention comprises an immuno assay as analytical method wherein the immuno assay is suitable to simultaneously measure the absence/presence (and, optionally, the concentration/amount etc.) of endogenous insulin and/or insulin analog(s), and endogenous GLP-1 and/or GLP-1 analog(s).

In this context, the term "simultaneous measurement" means that parameter(s) that correlate(s) with the presence/absence or concentration/amount of analyte(s) of interest of (a) fraction(s) of a fractionated sample is measured either at the same time for at least one different endogenous compound and/or its analogs, or that the fractions of a fractionated sample are used to measure a first parameter that correlates with the absence/presence or concentration/amount of the analytes of interest followed by a subsequent measurement of a second parameter that correlates with the absence/presence or concentration/amount of a different endogenous compound and/or its analog(s). In other words, the presence/absence or concentration/ratio of at least two different endogenous compounds and/or their corresponding analog(s) can be determined from one fractionated sample without having to split the obtained fractions.

As used herein, the term "pathologic condition" refers to non-healthy states that are caused by the absence/presence of hormones or hormone analogs that are involved in diabetes or in metabolic syndrome. The "pathologic" state as used herein can be a metabolic disease or an extrinsically pathological conditions (including death) caused by the administration of at least one of the hormone analogs. As non-limiting examples, a pathological condition comprises metabolic diseases such as diabetes (type I or II), metabolic syndrome, obesity, extrinsic pathologic conditions, i.e., a non-healthy state (including doping, hypoglycaemia factitia and death) caused by the administration of a dose or over-dose of at least one of the hormone analogs.

The term "diabetes" as used herein refers to diabetes mellitus and is a syndrome characterized by disordered metabolism and abnormally high blood sugar (hyperglycaemia) resulting from low levels of the hormone insulin with or without abnormal resistance to insulin's effects. Diabetes is a chronic disease that occurs when the pancreas does not produce enough insulin, and/or when the body cannot effectively use the insulin it produces. Hyperglycaemia, or raised blood sugar, is a common effect of uncontrolled diabetes and over time leads to serious damage to many of the body's systems, especially the nerves and blood vessels. The World Health Organization recognizes three main forms of diabetes mellitus: type 1, type 2, and gestational diabetes (occurring during pregnancy). While ultimately all forms are due to the beta cells of the pancreas being unable to produce sufficient insulin to prevent hyperglycemia, type 1 diabetes is usually due to autoimmune destruction of the pancreatic beta cells, type 2 diabetes is characterized by insulin resistance in target tissues. This causes a need for abnormally high amounts of insulin. Gestational diabetes is similar to type 2 diabetes in that it involves insulin resistance; the hormones of pregnancy can cause insulin resistance in women genetically predisposed to developing this condition.

A definition of the term "metabolic syndrome" as used herein is given by the International Diabetes Federation (IDF). Metabolic syndrome is related to diabetes. The term "metabolic syndrome" as used herein refers to a combination of medical disorders that increase the risk of developing cardiovascular disease and diabetes. Metabolic syndrome is also known as metabolic syndrome X, syndrome X, insulin resistance syndrome, Reaven's syndrome or CHAOS. Symptoms and features are fasting hyperglycemia (diabetes mellitus type 2 or impaired fasting glucose, impaired glucose tolerance, or insulin resistance); high blood pressure; central obesity, overweight with fat deposits mainly around the waist; decreased HDL cholesterol; and elevated triglycerides.

According to the International Diabetes Federation (IDF) definition for persons to be defined as having the metabolic syndrome as used herein they must have: central obesity (defined as waist circumference with ethnicity specific values) plus any two of the following four factors: raised triglyceride, reduced HDL cholesterol, raised blood pressure, raised fasting plasma glucose. The skilled reader will understand how to diagnose metabolic syndrome as used herein at a person by using the "IDF consensus worldwide definition of the metabolic syndrome", 2006.

The term "hypoglycaemia factitia" as used herein refers to episodes of low blood sugar caused by the administration of hormone analogs involved in diabetes and metabolic syndrome. Hypoglycaemia factitia can lead to death. In the latter case, the death can be, e.g., suicide, homicide or caused by dietary reasons.

The term "doping" as used herein refers to the use of performance-enhancing drugs, particularly those forbidden by organizations that regulate competitions.

The term "endogenous compound" as used herein refers to a compound that originate from within an organism, tissue, or cell. In other words, an endogenous compound is produced by an organism, tissue, or cell. The term encompasses peptides, proteins such as enzymes of the glycolysis pathway, saccharides such as glucose, nucleic acids, and metabolites such as hormones (e.g., peptide hormones, amino acid derivatives, isoprene derivatives, steroid hormones, eicosanoids). Embodiments of the present invention relate to methods for determining the presence/absence of analytes of interest, i.e., one endogenous hormone and/or analog(s) thereof that are involved in diabetes and/or metabolic syndrome. Notably, several embodiments of the present invention relate to methods wherein the simultaneous detection/analysis of the presence/absence or concentration/amount of further endogenous compounds and/or their analog(s) is preferred. In the latter embodiments, the different endogenous compound may be selected from, but not limited to the group consisting of a second endogenous hormone that is involved in diabetes and/or metabolic syndrome, an endogenous hormone that is not involved in diabetes and/or metabolic syndrome, a metabolite (such as a metabolite of the carbohydrate metabolism), a peptide, a protein, and a nucleic acid.

The terms "endogenous hormone involved in diabetes or metabolic syndrome" and "endogenous hormone" in the context of the present invention are used interchangeably and refer to a hormone that is produced by the body of an animal (including virus induced production), from which a sample to be separated and analyzed is obtained from an animal that is suspected to have a pathologic condition as defined herein. The endogenous hormone is involved in diabetes or metabolic syndrome, i.e., is involved in the signal pathway wherein the absence/presence/altered availability of these endogenous hormones results in one of these diseases or pathologic conditions. The term "endogenous hormone" as used herein also encompasses prohormones such as proinsuline. An endogenous hormone according to the present invention is preferably a peptide hormone. Non-limiting examples of endogenous peptide hormones involved in diabetes or metabolic syndrome are insulin, glucagon-like-peptide 1 (GLP-1), ghrelin, cholecystokinin (CKK), obestatin, and leptin.

In contrast, a "heterologous hormone" refers to an isoform/analog of an endogenous hormone which is a recombinant hormone, optionally chemically produced, produced as an endogenous hormone by another vertebrate, bird or an individual of the same species as the animal from which the sample to be separated and analysed is taken (e.g., a sample from an animal that is suspected to have a pathologic condition as defined herein) with the proviso that the heterologous hormone differs by at least one amino acid or at least one modification of an amino acid from the endogenous form of the animal.

The term "peptide hormone" as used herein refers to a class of peptides that have endocrine functions in living animals. A peptide as used herein refers to any entirety comprising at least one peptide bond, and can comprise either D- and/or L-amino acids. A peptide can have about 2 to about 250, preferably about 2 to about 150, more preferably about 2 to about 80 amino acids.

"insulin" is a peptide hormone composed of 51 amino acid residues causing liver and muscle cells to take in glucose and store it in the form of glycogen, and causing fat cells to take in blood lipids and turn them into triglycerides. In addition it has several other anabolic effects throughout the body. In mammals, insulin is synthesized in the pancreas within the beta cells ($\beta$-cells) of the islets of Langerhans.

insulin is used medically to treat some forms of diabetes mellitus. Patients with type 1 diabetes mellitus depend on external insulin (most commonly injected subcutaneously) for their survival because of the absence of the hormone. Patients with type 2 diabetes mellitus have insulin resistance, relatively low insulin production, or both.

The genetic structure of insulin varies marginally between species of animals. Insulin from animal sources differs somewhat in regulatory function strength (i.e., in carbohydrate metabolism) when used in humans because of those variations. Porcine (pig) insulin is especially close to the human version.

The "glucagon-like peptide-1" (GLP-1) is a gut peptide hormone derived from the transcription product of the proglucagon gene. The biologically active forms of GLP-1 are GLP-1-(7-37) and GLP-1-(7-36)$NH_2$. The secretion of GLP-1 is dependent on the presence of nutrients in the lumen of the small intestine. The secretagogues (agents that cause or stimulate secretion) of this hormone include major nutrients like carbohydrate, protein and lipid.

GLP-1 is potential candidate for the treatment of diabetes mellitus, since the physiological functions of GLP-1 include the increase of insulin secretion in a glucose-dependent manner, a decrease of glucagon secretion from the pancreas, the increase of beta cells mass and insulin gene expression, the inhibition of acid secretion and gastric emptying in the stomach and the decrease of food intake by increasing satiety.

"Ghrelin" is a hormone produced mainly by P/D1 cells lining the fundus of the human stomach and epsilon cells of the pancreas that stimulates appetite. Ghrelin levels increase before meals and decrease after meals.

Ghrelin and synthetic ghrelin mimetics (the growth hormone secretagogues) increase food intake and increase fat mass. They activate cells in the arcuate nucleus that include the orexigenic neuropeptide Y (NPY) neurones. Ghrelin-responsiveness of these neurones is both leptin and insulin sensitive.

Ghrelin levels in the plasma of obese individuals are usually lower than those in leaner individuals. Those suffering from the eating disorder anorexia nervosa appear to have high plasma levels of Ghrelin. These findings indicate that ghrelin does not cause anorexia or obesity, rather, ghrelin attempts to correct these disorders "Obestatin" is a hormone that was found to decrease appetite. Both obestatin and ghrelin are encoded by the same gene; the gene's product breaks apart to yield the two peptide hormones.

"Leptin" is a 16 kDa peptide hormone that plays a key role in regulating energy intake and energy expenditure, including the regulation (decrease) of appetite and (increase) of metabolism. Leptin is one of the most important adipose derived hormones.

Although leptin is a circulating signal that reduces appetite, in general, obese people have an unusually high circulating concentration of leptin. These people are believed to be resistant to the effects of leptin, in much the same way that people with type 2 diabetes are resistant to the effects of insulin. Thus, obesity develops when people take in more energy than they use over a prolonged period of time, and this excess food intake is not driven by hunger signals, occurring in spite of the anti-appetite signals from circulating leptin. The high sustained concentrations of leptin from the enlarged fat stores result in the cells that respond to leptin becoming desensitized.

"Cholecystokinin" is a peptide hormone of the gastrointestinal system responsible for stimulating the digestion of fat and protein.

A "hormone analog" as used herein is an altered form of an endogenous hormone secreted by the body of the animal from which the sample is taken. A hormone analog typically is still available to the animal's body for performing the same action as the endogenous hormone in terms of glycemic control. A hormone analog according to the present invention is normally produced outside the animal's body, i.e., a heterogenous hormone, and subsequently administered to the animal. For example, a hormone analog my be orally administered, given by injection into a vein (intravenously), into a muscle (intramuscularly), or beneath the skin (subcutaneously); placed under the tongue (sublingually); sprayed into the nose and absorbed through the nasal membranes (nasally); breathed into the lungs, usually through the mouth (by inhalation); applied to the skin (cutaneously); or delivered through the skin by a patch (transdermally).

A hormone analog as used herein comprises any stereoisomer, substituted form, isoform and/or any form comprising an addition, replacement, deletion, or chemical modification of one or more amino acids compared to the endogenous hormone.

If the endogenous hormone is a peptide hormone, the amino acid sequence of the hormone analog may differ from the amino acid sequence of an endogenous hormone, i.e., the amino acid sequence may contain one or more amino acid mutations; the hormone analog may be comprised of a shortened (deletion form) or elongated (addition form) amino acid chain, e.g., by a posttranslational modification; and/or may differ by a modification of at least one amino acid (e.g., substitution of an amino acid). The skilled person will understand that a peptide hormone may consist of one, two or more than two interacting amino acid chains.

A non-limiting example is a recombinant peptide hormone wherein the amino acid sequence of an endogenous hormone was changed to alter its absorption, distribution, metabolism, and excretion characteristics through genetic engineering of the underlying DNA.

The term "hormone form" as used in the context of the present invention encompasses endogenous hormones and heterologous hormones thereof (i.e. an isoform thereof, an analog thereof, a prohormone, an isoform or an analog of a prohormone).

A "mutation" as used herein refers to the replacement of an amino acid of the endogenous form against a different amino acid. In certain embodiments, the amino acid sequence of the hormone analog(s) differs from the endogenous hormone by the mutation of 5 or more, preferably at most 5, at most 4, at most 3, at most 2 or 1 amino acid(s). If more than one of the amino acids is mutated, two or more mutated amino acids may be located adjacent to each other or the mutated amino acids may be separately located on the amino acid chain(s).

Furthermore, the amino acid sequence of a hormone analog may comprise 5 or more, preferably 4, 3, 2 or 1 amino acids more (addition form) or 5 or less, preferably 4, 3, 2 or 1 amino acids less (deletion form) compared to the amino acid sequence of the endogenous hormone.

A "modification of an amino acid" as used herein refers to amino acids that may carry a substituent normally absent from the amino acid. A hormone analog may differ from an endogenous hormone by a modification of at least 1, at least 2 or even 3 or more amino acid(s). Non-limiting examples for a substituent of an amino acid are a $C_1$-$C_{20}$ saturated or unsaturated fatty acid, a $C_1$-$C_{20}$ alkyl, $C_1$-$C_{20}$ alkanoyl, a mono-, di-, tri- or polysaccharide(s), phosphates, sulfonates, sialyl residues and the like. A modified hormone analog may optionally comprise one or more mutations in the amino acid chain.

The "primary structure" of a peptide hormone as used herein refers to the sequence of the amino acids along its backbone, i.e. an amino acid chain. The primary structure in the context of the present invention does not comprise the retention of cross-linking bonds, most commonly by disulfide bonds, i.e., the primary structure as used herein does not require specifying the cross-linking atoms (e.g., specifying the cysteines involved in the protein's disulfide bonds). In hormones that are not peptide hormones, the primary structure relates to the carbon backbone of a molecule.

An "analyte of interest" in the context of the present invention is an endogenous hormone or a hormone analog thereof that is present in a sample and wherein the endogenous hormone is involved in diabetes or metabolic syndrome. Accordingly, the term "analytes of interest" includes any hormone analog form of the endogenous hormone in a sample. As a non-limiting example, a sample may comprise the endogenous hormone human insulin and the analogs insulin Aspart and insulin Glulisine. Each of these compounds is an analyte of interest. In certain embodiments of the present invention, an endogenous hormone or an analog thereof is expected to be comprised by a sample. In such embodiments, the hormone form is also encompassed by the term analyte of interest although it may in reality not be present in the sample. For example, the sample of a diabetes patient who is suspected to have administered insulin Aspart should thus contain insulin Aspart. Accordingly, one would expect the analog to be present in the sample, measuring the fractions wherein the analog will normally be eluted from a separation apparatus.

Furthermore, it will be understood that an endogenous hormone "involved in diabetes or metabolic syndrome" may mean that the absence of the endogenous hormone in an animal's body causes or is caused by the syndrome, e.g. diabetes type 1.

The term "sample" as used herein comprises at least two analytes of interest (an endogenous hormone and/or analogs thereof) which are sufficiently soluble in a separation medium according to embodiments of the present invention and which are to be quantitatively separated prior to an analytical method. The samples employed in the methods and devices of the present invention may be obtained from, but are not limited to, the group consisting of blood, plasma, serum and urine of an animal.

The term "animal" as used herein comprises birds and vertebrates, preferably mammals.

As used herein, "mammal" refers to any animal classified as a mammal, including humans, domestic and farm animals, as well as zoo, sports, or pet animals, such as dogs, horses, cats, sheep, pigs, cows, etc. The preferred mammal herein is a human.

An "extensive sample preparation" as used herein means any step that leads to an modified sample composition such as buffer exchange steps, purification steps and the like. Notably, an "extensive sample preparation" as used herein does not comprise simple steps such as centrifugation of a blood sample and, optionally, addition of EDTA to obtain a serum or plasma sample, respectively, and/or dilution of a sample with a separation buffer as used in the subsequent separation method (i.e., step (a) of the methods described herein). Thus, the term "extensive sample preparation" as used herein would comprise a pre-purification of the analytes of interest from abundant compounds such as albumin by an affinity chromatographic step that retains all analytes of interest without separating them from each other, or by an affinity chromatographic step to retain an analyte (e.g. a protein or metabolite) that is not an analyte of interest, or by precipitation, a buffer exchange step and the like.

The term "concentration of a sample" as defined herein means a reduction of a sample volume of a fraction derived from step (a) by evaporation of the solvent by, e.g., lyophilisation, by using a Speed Vac or gentle heating at ambient temperatures that do not destroy the analytes of interest. In other words, "evaporation" is notably different from eliminating solvent or other compounds comprised in a fraction by techniques commonly referred to as affinity chromatography, a buffer exchange step (sometimes also referred to as "desalting") including column chromatography and dialysis, cut-off filtration methods, techniques known as solid phase extraction or precipitation of analytes of interest or of further analytes that are not analyzed further.

A "buffer exchange step" as used herein refers to an exchange or removal of compounds from a sample which are not the solvent or an analyte of interest. As stated above, the centrifugation and, optionally, addition of EDTA is not encompassed by this term. It will be understood that a(n) (affinity) chromatography to exchange a medium with a different medium is also encompassed by the term "buffer exchange step", provided that it does not quantitatively separate at least those analytes of interest from each other whose common presence in the same fraction would interfere with the measurement of a parameter of one of the analytes of interest by a subsequent analytical method. A buffer exchange step that can be avoided prior or subsequent to a separation step comprised in a method according to aspects of the present invention encompasses steps such as gel filtration chromatography, dialysation, ultrafiltration, affinity chromatography (in view of the analytes of interest or in view of a different compound) and the like.

Notably, the term "buffer exchange step" as used herein does not relate to an exchange of the medium comprising an analyte of interest during the separation step. The term "medium" in this context of the present invention refers to any medium, including separation buffer medium, plasma, serum, combination thereof and the like. For example, several embodiments of FFE allow a convenient buffer exchange during the separation phase, i.e., a separated analyte of interest can be eluted from a separation zone in a specific buffer medium different from the sample buffer medium, and different from the separation buffer medium into which the analyte of interest was introduced into the separation device.

A "fractionated sample" in the context of the present invention means a sample wherein the various analytes of interest in the sample are separated during a separation method such as electrophoresis, preferably capillary electrophoresis or free flow electrophoresis (FFE) and wherein the sample can thus be divided into several fractions after the separation step. Those of skill in the art will understand how to collect individual fractions which exit the separation chamber of an apparatus suitable for FFE through multiple collection outlets and are generally led through individual tubings to individual collection vessels of any suitable type (e.g., 96 well plates, and sometimes plates of different sizes, e.g., 144, 288, 576 or even more wells).

Optionally, the fractions are not collected, but the presence/absence, concentration and/or amount of an analyte of interest is measured online by measuring a parameter that correlates with the presence/absence, concentration and/or amount of an analyte of interest in at least those fractions of a fractionated sample wherein the analyte of interest is predicted to elute from a separation zone. Notably, the measurement of the parameter can also occur if the analyte of interest is not present in a sample.

The term "online" as used in the context of the present invention refers to a measurement of a parameter of a fraction of a fractionated sample that correlates with the presence/absence, concentration or amount of an analyte of interest, wherein the fraction is not collected subsequent to the separation method but the parameter is measured while the fractionated sample flushes through an analytical device suitable to perform an online detection. A non-limiting example for online detection in the context of the present invention is a coupled free flow electrophoresis-surface plasmon resonance method (FFE-SPR), wherein the separated analytes separately flushes over a biosensor of an SPR device. More specifically, a coupled FFE-SPR for analysing insulin and/or insulin analog(s), wherein the SPR-biosensor having separated flow channels has at least an area on its surface covered with a cross reactive insulin antibody and, optionally, further comprises an area with an insulin Lispro specific antibody, wherein each flow channel separately crosses both areas. As will be understood by the skilled person, such an online detection device is also suitable to simultaneously detect/analyse further endogenous compounds and/or their analog(s), depending on the number of coating areas in each flow channel of the biosensor, i.e., such a biosensor can be used as an online multiplexing array.

The terms "quantitative separation" and "quantitatively separated" as used herein are intended to mean an essential separation of the endogenous hormone and/or analogs thereof from each other during the separation procedure. Essential separation is to be understood as a separation of the endogenous hormone and/or analogs thereof from each other, wherein not more than 10%, preferably not more than 5%, more preferably not more than 2% or not more than 1% of one of the analytes of interest is present in a fraction wherein another separated analyte of interest is the abundant analyte of interest. In other words, the amount of the abundant analyte of interest in a fraction that may comprise more than one analyte of interest makes up more than 90%, preferably more than 95%, more preferably more than 98% or more than 99% of the total amount of analytes of interest in said fraction. In most preferred embodiments, the separation achieves an isolation of the analytes of interest from each other, i.e., fraction(s) containing one analyte of interest do(es) not contain another analyte of interest.

The skilled person will understand that at least the analytes of interest (the hormone analog(s) and/or the endogenous hormone) whose common presence in a fraction of a fractionated sample interferes with measuring a parameter of one of the analytes of interest by an analytical method employed in step (b) are separated, preferably isolated from each other in step (a) of a method according to embodiments of the present invention. An isolation of two analytes of interest is achieved if a silver stained gel of a separation of standards of two analytes of interest shows at least one fraction that is located between fractions individually containing the analytes of interest and that shows no stained band(s) indicating an overlapping of the elution profiles of the analytes of interest. Such a silver stained gel may, e.g., be prepared by separating standards of the analytes of interest in a medium that is equal to a sample. For example, standards of two insulin analogs can be mixed with human serum that does not contain the analogs or, preferably, no insulin form at all if the sample is a human serum sample. The skilled person will further understand that the evaluation of the presence and amount of an analyte of interest in a fraction can be achieved by individually running standards of the analytes of interest and measuring the amount of an analyte of interest in a fraction with potential overlapping elution profiles of two analytes of interest by, e.g. ELISA or mass spectrometry.

The separation technique to quantitatively separate at least two analytes of interest according to aspects of the present invention may be any separation technique that allows at least the separation of any analytes of interest (the hormone analog(s) and/or the endogenous hormone) from each other whose common presence in the same fraction(s) of a separated sample interferes with measuring a parameter of one of the analytes of interest by an analytical method employed in step (b) of the methods described herein. For example, suitable separation methods include electrophoretic methods.

The term "parameter of" an analyte of interest as used in the context of the present invention is to be understood as a measurable signal that correlates with the presence/absence and/or concentration/amount of an analyte of interest in a fraction. The parameter to be measured of an analyte of interest may be a parameter that directly correlates with the analyte of interest, e.g. the parameter is the absorption or emission of radiation caused by the analyte of interest, or that indirectly correlates with the analyte of interest, e.g., the parameter is radioactivity or emitted radiation caused by chemiluminescence, wherein the source of the signal is caused by an antibody that interacts with the analyte of interest (immuno assay).

The term "electrophoretic separation" as used herein refers to a technique that can be used to separate charged or ionic species by their behaviour (caused, e.g., by their charge and/or electrophoretic mobility) in an electrical field. Electrophoretic separationcomprises techniques such as gel electrophoresis, capillary electrophoresis and free flow electrophoresis.

"Capillary electrophoresis" includes free-solution and matrix-based (i.e. gel) capillary electrophoresis. The flow direction of the analytes in the capillary is parallel to the streamlines of the applied electrical field.

"Free flow electrophoresis" (FFE) as used herein is a technique wherein the separation of analytes occurs in liquid medium in the absence of a stationary phase (or solid support material). FFE is often referred to as carrier-less deflection electrophoresis or matrix-free deflection electrophoresis. The FFE separation may principally be carried out in a preparative manner so that certain fractions are subsequently collected, or may merely be carried out analytically, where the analyte of interest or its presence in a certain fraction is merely detected by suitable means, but not collected, e.g., for further use. In contrast to capillary electrophoresis, wherein the flow direction of the separation media is the same as the streamlines of the applied electrical field, the flow direction of the separation media in free flow electrophoresis is perpendicular to the streamlines of an applied electrical field and allows, e.g., the separation of the analytes in different separation media.

The FFE principle is based on a electrophoretic separation process in a thin layer of buffers flowing through a flat chamber in a laminar fashion. The absence of any kind of solid separation matrix prevents unspecific adsorption of analytes and allows fast and native separation conditions.

The term "separation zone" of an apparatus suitable to perform a separation method describes the area where the actual separation of the analytes is carried out.

In embodiments of the present invention where the separation technique is free flow electrophoresis (FFE), the term "separation zone" as used herein should be understood to be located between the two elongated electrodes of an apparatus suitable to perform a free-flow electrophoretic separation. A separation zone is formed by at least one separation buffer medium. A separation zone may comprise more than one separation buffer media, whereof one or more separation buffer media may act as a focus medium. Optionally, a separation zone may additionally comprise stabilizing media. In some embodiments, a focus medium acts as a stabilizing medium. Typically, a separation zone is encompassed on each side by an electrode medium (see FIG. 1). In some embodiments, a stabilizing medium may also act as an electrode medium. In the latter case, a separation zone may also encompass an electrode medium.

A "separation buffer medium" (SBM) as used herein refers to a mixture of mono, di- or tri-protic/basic compounds (buffer compounds), which are able to maintain a solution at an essentially constant pH value upon addition of small amounts of acid or base, or upon dilution. At least two buffer compounds form a buffer system within a medium. The combination of separation buffer media within a separation zone is suitable to perform a free flow electrophoretic method. Such a method may be carried out in an operation method selected from but not limited to zone electrophoresis (ZE), isoelectric focusing (IEF) or combinations thereof, comprising, e.g., pH plateaus as described in International patent application PCT/EP2007/056167, which is hereby incorporated by reference in its entirety, or isotachophoresis (ITP). Depending on the FFE separation method, the separation of at least one analyte to be separated relies on the pI or its electrophoretic mobility. Non-limiting examples for suitable categories of buffer systems are commercially available ampholytes, complementary multi-pair buffer systems (CMPBS), volatile buffer systems or binary buffer systems (NB buffer systems).

The term "focus medium" as used herein refers to a SBM comprising an acid for an anodic focus medium or a base for a cathodic focus medium which form a conductivity step and, optionally, a pH step regarding the adjacent SBM. A focus zone formed by at least one SBM reduces the movement of analytes towards the anode or cathode essentially to zero due to a conductivity step. Such a conductivity step can be achieved by adding a strong acid or strong base to the SBM forming the focus zone. The concentration of the acid and base will be chosen so as to be sufficient to increase the conductivity of the at least one SBM focus medium, preferably by a factor of at least 2, and more preferably of at least 3, at least 5, or even more with regard to an adjacent SBM. This abrupt increase in the electrical conductivity of the medium is useful to accumulate analytes with a different pI as the pH range of the SBMs at the border of the two media having different conductivity values since the mobility of analytes moving to the anode or cathode, respectively is reduced to essentially zero. The principles of "focus media" are described in, e.g., International patent application PCT/EP2008/050597 and U.S. Pending Provisionals U.S. Ser. Nos. 60/945,246 and 60/987,208, which are incorporated herein by reference in their entirety. It will be understood that a focus zone is generally formed by one focus medium, i.e., by one SBM but can also be formed by more than one SBM.

In certain embodiments, the pKa value of the acid in the anodic focus medium will be selected to be lower than the pKa value of the acid employed in the adjacent pH function, pH gradient or pH separation plateau (i.e. a stronger acid is selected for the anodic focus medium). In certain embodiments of the present invention, the pKa difference is greater than about 1 pH unit, preferably greater than about 2 pH units, and most preferably even greater than about 3 pH units. Suitable examples for an acid used to increase the conductivity is selected from, but not limited to the group consisting of sulfuric acid, pyridine-ethanesulfonic acid, hydrochloric acid, phosphoric acid, trifluoroacetic acid, trichloroacetic acid, and formic acid. An anodic focus medium may comprise the acid responsible for the increased conductivity and additionally the buffer compounds of an adjacent separation buffer medium, a volatile buffer system, a binary buffer acid/buffer base system (A/B medium), a commercially available ampholytes, a complementary multi pair buffer system (CMPBS) and/or a weak base to regulate the pH of the focus medium. A weak base should be understood to have a pKa that is lower than the pKa of the base used in the adjacent separation buffer medium.

The same principles apply mutatis mutandis to the selection criteria for the base in the cathodic focus medium. Accordingly, the pKa value of the base in the cathodic focus medium will be selected to be higher than the pKa value of the base employed in the adjacent pH function, pH gradient or pH separation plateau (i.e. a stronger base is selected for the cathodic focus medium). In certain embodiments of the present invention, the pKa difference is greater than about 1 pH unit, preferably greater than about 2 pH units, and most preferably even greater than about 3 pH units. Suitable examples for a base used to increase the conductivity is selected from, but not limited to the group consisting of alkali or earth alkali hydroxides such as sodium hydroxide, 3-morpholino-2-hydroxy-propansulfonic acid, Tris, and the like. A cathodic focus medium may comprise the base responsible for the increased conductivity and additionally the buffer compounds of an adjacent separation buffer medium, a volatile buffer system, a binary buffer acid/buffer base system (A/B medium), a commercially available ampholytes, a complementary multi pair buffer system (CMPBS) and/or a weak acid to regulate the pH of the focus medium.

By virtue of its high electrical conductivity and its composition, a focus medium may also act as a stabilizing medium.

"Stabilizing media" used for methods according to embodiments of the present invention have been described in co-pending PCT application PCT/EP2008/050597, which is incorporated herein by reference in its entirety. The stabilizing media are useful and suitable for stabilizing the conditions within the separation zone. A suitable stabilizing medium thus also acts as a "reservoir" supplying or replacing the ions in the separation zone.

The isoelectric point (pI) is the pH at which a particular molecule or surface carries no net electrical charge. Amphoteric molecules called zwitterions contain both positive and negative charges depending on the functional groups present in the molecule. They are affected by the pH of their surrounding environment and can become more positively or negatively charged due to the loss or gain of protons ($H^+$). A molecule's pI can affect its solubility at a certain pH. In general, the pI of a certain analyte must be either known or must be identified by means known to those of skill in the art. One possible way to determine the pI of a given analyte of course includes the determination by a suitable FF-IEF technique.

The electrophoretic mobility EM (or $\mu_e$) is defined as the coefficient between particle speed (V) and electric field strength (E):

$$\mu_e = \frac{v}{E}$$

The determination of the electrophoretic mobility EM can be easily carried out using techniques that are well-known to those skilled in the art.

The term "denaturing", as used herein, refers to a process in which the native conformation of an analyte (three-dimensional structure) is changed but the primary structure (e.g., amino acid chain, peptide links) of the analyte remains unchanged, i.e., "denaturing conditions" refer to those conditions that disrupt the tertiary and/or quaternary structure of the target molecule.

The term "denaturant" as used herein refers to an agent, in the presence of which (normally in solution) the native conformation of an analyte is not preserved. Biological activity of, e.g., proteins in the presence of denaturants is typically changed and in most instances not preserved.

The term "non-denaturing conditions" as used herein refers to conditions such that denaturing of an analyte to be separated does not occur. These conditions refer to, e.g., conditions where no denaturant is present or is present below denaturing concentrations.

The term "native conditions" as used herein refers to conditions in which an analyte to be separated can preserve the native conformation and in case of a protein the biological activity, i.e., "native conditions" refer to those conditions under which an analyte to be separated maintains its normal tertiary and quaternary structure.

The terms "zone I" and "zone II" as used herein in the context of FFE refer to areas within a separation zone which are formed by at least one SBM type I or type II, respectively.

The term "transferring" as used in the context of the methods according to embodiments of the present invention refers to the fact that at least one analyte of interest is introduced together with a SBM type I or into a zone I formed by at least one SBM type I and moves during an FFE separation into a zone formed by at least one SBM of type II or vice versa according to its pI or electrophoretic mobility (i.e. from a SBM type II/zone II into a zone I).

A "SBM type I" as used herein refers to a SBM comprising at least one additive at an effective concentration, which is not present in a "SBM type II".

Accordingly, a "SBM type II" refers to a SBM which does not contain an additive at an effective concentration that is comprised in a SBM type I, i.e., the additive may be typically present in a SBM type II below an effective concentration and will preferably not be present in a SBM type II, i.e., a SBM is typically produced without said additive.

In certain embodiments, as will be known by the skilled person, minor contaminants of the additive may move from a SBM type I into a SBM type II during electrophoretic separation, depending on the diffusion rate, the charge or electrophoretic mobility of the additive. Such minor contaminants below the effective concentration are still included under the definition of a SBM type II of the present invention.

In preferred embodiments, the additive is absent in a fraction comprising at least one analyte of interest which is transferred during FFE separation from one SBM type into another SBM type, i.e., the concentration of the additive in a fraction comprising at least one analyte of interest and a SBM type II is below the detection limit.

In certain embodiments, wherein an additive at an effective concentration in a SBM type I is present in a minor concentration in a SBM type II fraction subsequent to an FFE separation, the concentration ratio between the additive in the fraction and the concentration of the additive in the SBM type I prior to the FFE separation method is $\leq 0.5$, $\leq 0.2$, $\leq 0.1$, $\leq 0.05$, preferably $\leq 0.01$, more preferably $\leq 0.001$ and most preferably $\leq 0.0001$.

In certain embodiments, a minor concentration of the additive may be present in a SBM type II before or subsequent to an FFE step but in a concentration below the effective concentration. In such a case, the concentration is in a range wherein the effect caused by the effective concentration of the additive is not exhibited in a SBM type II compared to a SBM type I. As an example, an "additive at an effective concentration" may be a denaturant. In a SBM type I, the denaturant is present in an effective concentration to exhibit denaturing conditions in regard of at least one analyte of interest, whilst the denaturant is present in a SBM type II in a concentration that essentially does not lead to the disruption of the tertiary and/or quaternary structure of the at least one analyte of interest. The skilled person knows how to determine the tertiary and/or quaternary structure of a protein using, e.g., circular dichroism. In the latter case, it is irrelevant whether the minor concentration of the denaturant was present in SBM type II before the SBM type II entered the separation chamber of an FFE apparatus or whether the minor concentration stems from a migration of the denaturant from a SBM type I into a SBM type II during the FFE step.

The principle underlying this aspect of the present invention relates to the presence/absence of at least one additive at an effective concentration. In embodiments, wherein the additive should be present in a SBM type II prior to an FFE separation in a concentration below the effective concentration, the concentration ratio of the additive in a SBM type II and a SBM type I is below $\leq 0.5$, $\leq 0.2$, $\leq 0.1$, $\leq 0.05$, preferably $\leq 0.01$, more preferably $\leq 0.001$ and most preferably $\leq 0.0001$.

The skilled person will understand that additive are present in a SBM to provide a desired effect, e.g., denaturing conditions/native condition, enhanced/reduced viscosity, enhanced/reduced surface tension, inhibition of an enzyme activity, etc. It will be understood that the effect is caused by the presence of an additive at an effective concentration. The skilled person will be well aware of desired/undesired effects that are caused by the absence (or presence below an effective concentration) or by the presence of the additive at an effective concentration.

The underlying idea of this aspect of the present invention is the provision of a fraction comprising an analyte after a FFE separation, wherein the SBM of the fraction possesses a desired effect/advantageous property compared to the SBM of a different type. In other words, the effect/property is based on the absence/presence of the additive at an effective concentration compared to a SBM that comprises/does not comprise the additive at an effective concentration.

It will be understood in the context of the present invention that the additive is not part of the buffer system forming the separation buffer medium and is not meant to include a strong acid or a strong base. For example, a method according to embodiments of the present invention therefore allows avoiding a buffer exchange step subsequent to the FFE step and prior to further analysis steps or prior to storage by combining a separation and a buffer exchange step.

A desired effect caused by the additive depends in general on the concentration, i.e., the "effective concentration", of the additive within a medium. Furthermore, the common knowledge of a skilled person enables the skilled person to determine the concentration of an additive at which a desired effect occurs. The skilled person is well aware of methods how to determine the effective concentration of an inhibitor (e.g., the "additive at an effective concentration" is an inhibitor such as a protease inhibitor present in a SBM type I and not present at all in a SBM type II, or merely present in a SBM type II in minor concentrations caused by its movement in an electrical field or by migration from SBM type I into SBM type II during the FFE separation, or present in a concentration below the effective concentration in an SBM type II before the FFE separation) for example via state-of-the-art enzymatic activity tests, or how to determine the effective concentration of a denaturant in view of at least one analyte of interest (e.g., the "additive at an effective concentration" is a denaturant such as urea or thiourea present in a SBM type I and not present at all in a SBM type II, or merely present in a SBM type II in minor concentrations caused by its movement in an electrical field or by migration from SBM type I into SBM type II during the FFE separation, or present in a concentration below the effective concentration in an SBM type II before the FFE separation) for example via circular dichroism.

The term "interaction partner" as used herein refers to an analyte that is not an analyte of interest and that interacts under certain conditions via a at least one covalent bond, ionic interactions, an interaction caused by van der Waals forces, a coordinative bond, any other affinity or any combination thereof with at least one analyte of interest, thereby forming an analyte-interaction partner-complex that yields a different behavior, e.g., a different charge and/or a different electric mobility, compared to the "free analyte of interest".

The term "free analyte" as used herein refers to an analyte of interest which does not interact with an interaction partner of an analyte-interaction partner-complex, or which does not interact under specific separation conditions (e.g., of a SBM medium type I) with an interaction partner of an analyte-interaction partner-complex, or which would interact with an interaction partner in case the interaction partner is present, i.e., in the latter case, the free analyte is the analyte of a possible analyte-interaction partner-complex without the interaction partner.

The terms "pH separation plateau" and "pH plateau" are used interchangeably herein. A pH plateau is essentially formed by one medium introduced into one inlet of an apparatus suitable for FFE, although it will be understood by those of skill in the art that more than one inlet of an FFE apparatus can be used to create the plateau. Although the pH range of the separation plateau has ideally a range of zero (i.e., it is essentially flat having a constant pH that essentially corresponds to the pI of an analyte to be separated from at least one, preferably all, analyte(s) of interest), a typical range may be such that the zone includes an upper and lower pH limit depending from, e.g. the surrounding separation/focus media (i.e., forming an essentially extremely flat pH gradient).

The analyte to be separated will have a pI which results in the absence of any net charge at the average pH of the pH separation plateau, thereby causing no migration in the electrical field. In general, the pI of a certain analyte must be either known or must be identified by means known to those of skill in the art. One possible way to determine the pI of a given analyte of course includes the determination by a suitable FF-IEF technique.

A slight shift to higher pH values at the cathodic side of the pH separation plateau and a shift to lower pH values on the anodic side (dependent of the surrounding media) will usually, but not necessarily, be observed. Thus, the fractions recovered from the anodic side of the pH separation plateau will often be referred to as the acidic pool and the fractions recovered from the cathodic side of the pH separation plateau will often be referred to as the alkaline pool.

In general, the pH separation plateau encompasses a pH range of a maximum of 0.4 pH units or less, preferably 0.3 pH units or less and more preferably a pH range of 0.1 pH units or less. In embodiments where the analyte is a protein, the separation may be performed in its native state or denatured state. For example, to separate native human serum albumin (HSA), a pH range of 4.7 to 5.0 is desirable, and a pH range of 4.8 to 4.9 is even more desirable in order to separate the protein from analytes of interest in a sample having a pI different from the pI of HSA, which is between 4.8 and 4.9.

In certain embodiments of the present invention, it may be advantageous to use specific buffer systems to prepare each SBM for free flow electrophoresis and/or capillary electrophoresis. As non-limiting examples, a SBM may comprise commercial ampholytes as a buffer system, a volatile buffer system, a binary buffer acid/buffer base system (NB medium), or a complementary multi pair buffer system (CMPBS).

Volatile Buffer Systems

"Volatile buffer" systems can be used as a buffer system of at least on separation buffer medium. These buffer systems are disclosed in U.S. Provisional Ser. No. 60/945,246 and U.S. 60/987,208 and offer the particular advantage that they can be removed residue-free from the recovered fractionated sample after an FFE separation step or are MS-compatible per se and can remain in the sample.

A volatile buffer system comprises at least one buffer acid and at least one buffer base, wherein all of the buffer compounds are volatile. Optionally, at least one of the buffer compounds may be capable of functioning as a (volatile) matrix for mass spectrometry, particularly in MALDI applications.

The term "volatile" used in connection with the buffer compounds herein should be understood to refer to the buffer compound's ability to be completely removable from an aqueous sample under suitable conditions, i.e., the buffer compound can be evaporated without leaving behind any residual compound (e.g., a salt), i.e. residue-free. In its broadest meaning, a volatile buffer compound can be removed residue-free under conditions selected from, but not limited to, the group of reduced atmospheric pressure, increased temperature, supply of energy by irradiation (e.g. UV light, or by applying a laser light), or any combination thereof, although it will be appreciated that a volatile buffer compound must essentially be non-volatile under FFE working conditions (i.e., atmospheric pressure and temperature ranges of typically between 0 and 40° C. as explained hereinabove).

In this context, the skilled person will understand that, in one embodiment of the invention, the analyte(s) that is (are) present in a sample comprising volatile buffer compounds will be non-volatile under the afore-mentioned conditions, i.e., the analyte(s) is (are) essentially not modified (e.g., by fragmentation or oxidation) and remain(s) in solution or in its (their) solid state. In certain embodiments, particularly under mass spectrometric working conditions, the analyte(s) will also be volatile and will be ionizable (required for detection by MS).

The term "non-volatile under FFE working conditions" as used herein means a volatility of a buffer compound leading to a concentration reduction of the respective buffer compound in the separation medium of less than 5% w/v or, preferably less than 2% w/v under working conditions and during the separation period of FFE. Most preferably, no concentration reduction will be observed at all under working conditions and the separation period of FFE.

The term "residue-free" as used herein means that the volatile compound itself evaporates completely, but that residues caused, e.g., by an impurity of the used substances, may be non-volatile. However, it is well known to those of skill in the art that only compounds having the highest purity grade available should be used for analytic purposes, and particularly so for mass spectrometric analysis.

Removal of the solvent and buffer compounds by "evaporation" as used herein should be understood to refer to a removal from the analytes of interest through transferring the compounds into the gas phase and subsequent elimination of the gas phase by suitable means. Thus, evaporation as defined herein is different from eliminating the buffer compounds by techniques commonly referred to as buffer exchange (sometimes also referred to as "desalting"), including column chromatography, dialysis or cut-off filtration methods, or techniques known as solid phase extraction or analyte precipitation. Alternatively, in certain applications that are not included under the term evaporation, the buffer compounds present in salt form are simply washed away with water, although this obviously leads to an undesirable loss of sample material and, moreover, non-quantitative removal of the buffer compounds. Those of skill in the art will appreciate that the volatile buffer compounds as defined herein could, at least in principle, likewise be removed by such buffer exchange or solid phase extraction techniques, although this would of course neglect the distinct advantage offered by the volatility of the buffers (and makes no sense in view of the potential problems connected with buffer exchange techniques, e.g., difficult handling and low sample recovery).

Suitable exemplary techniques for removing the solvent and the volatile buffer compounds from a sample collected from an FFE separation step by evaporation include, but are not limited to, vacuum centrifugation using suitable devices such as a centrifugal evaporator or a vacuum centrifuge known for example under the name SpeedVac®, by lyophilization or by a (gentle) heating of the aqueous sample. Other possibilities to evaporate the solvent and the buffer compounds include evaporation by subjecting the sample to reduced pressure conditions, e.g., applying a vacuum to the sample placed on a target plate used in mass spectrometric analysis. Those of skill in the art will appreciate that most mass spectrometric methods operate under vacuum conditions (for example vacuum MALDI) so that the volatile buffer compounds are conveniently removed after the introduction of the sample into the MS instrument, but prior to ionization.

Preferably, the volatile buffer compounds are removable under conditions of reduced pressure and/or increased temperature. Moreover, in other embodiments, the volatile buffer compounds may even be evaporated under ambient temperature and atmospheric pressure conditions, particularly if the volatile buffer-containing sample is present in a small volume (e.g., for mass spectrometric analysis). However, in most cases at least some buffer solution will not evaporate readily under those conditions. In yet other embodiments, the volatile buffer compounds can only be removed under harsher conditions (e.g., in vacuum and/or high temperatures, optionally with irradiation, such as under mass spectrometric working conditions).

In certain embodiments of the present invention, the FFE separation media comprise volatile buffer compounds wherein at least one of the volatile buffer compounds may act as a (volatile) matrix for mass spectrometric analysis, i.e., the compound can only be removed under mass spectrometric working conditions. It will be understood that the term matrix in the context of mass spectroscopy (MS) as used herein is different from the term "matrix" used in the context of electrophoresis (e.g., polyacrylamide or agarose). Therefore, in some embodiments wherein the downstream analysis is for example a MALDI application, a matrix component for MALDI analysis is added to the analyte buffer solution prior to mass spectrometric analysis.

Examples for volatile buffer systems include, but are not limited to combinations of TRIS/acetic acid, diethanolamine/picolinic acid, dimethylamino-proprionitril/acetic acid, 2-pyridine ethanol/picolinic acid, benzylamine/2-hydroxypyridine, tri-n-propylamine/trifluoroethanol, and the like.

Complementary Multi-Pair Buffer Systems (CMPBS)

In certain embodiments of the invention, a buffer mixture used to generate the pH gradient may be comprised of carefully matched acids and bases such that the mixture may provide a smooth pH gradient when current flows through the buffer system. A mixture of low molecular weight organic acids and bases are chosen that enable an increased buffering capacity compared to commercially available high molecular weight ampholytes. These mixtures of carefully matched acids and bases are extremely well characterized in terms of molecular weight, pI, purity, and toxicity. Generally, the acids and bases have a smaller molecular weight than those of commercial ampholytes. Suitable complementary multi-pair buffer systems are known in the art. Specifically, a mixture with a pH range from 3 to 5 is sold as BD FFE Separation medium 1 while a mixture with a pH range from 5 to 8 is sold as BD FFE Separation medium 2 by BD GmbH Germany. These buffer systems have, for example, been described in general form in US patent application US 2004/0101973 and in EP 1 320 747 which are incorporated herein by reference in their entirety. Complementary multi-pair buffer systems as described above are referred herein as "CMPBS" or "CMPBS media".

Binary Buffer Systems (A/B Buffer System)

Binary buffer systems as defined below are referred to herein as "NB buffer systems" and are disclosed in detail in International patent application PCT/EP2008/050597, which is incorporated herein by reference in their entirety. The buffer system comprises at least one buffer acid and at least one buffer base, with the proviso that the pKa value of the buffer acid must be higher than the pH of the SBM and the pKa of the buffer base is lower than the pH of the SBM. Put another way, the pKa of the buffer acid will be higher than the pKa of the buffer base.

The pH profile exhibited by the NB SBM may be essentially linear (i.e., without any major pH steps during electrophoretic separation). Depending on the stabilizing media employed as well as the pKa differences between the buffer acid and the buffer base, the A/B SBM according to this aspect of the invention will offer an essentially constant (i.e., flat) pH profile, or a rather gentle/flat pH gradient within the separation chamber. It will be appreciated that the separation media providing a zone with an essentially constant pH in the separation chamber between the electrodes are particularly useful for the creation of pH separation plateaus in accordance with the methods described herein. However, since the NB SBM may also form flat- or ultra flat pH gradients, they can also be used for the creation of pH functions or pH gradients as defined herein.

Preferably, the A/B SBM employing at least one buffer acid and one buffer base in accordance with the above aspect of the present invention are characterized by a pKa difference between the at least one buffer acid and the at least one buffer base of between about 0.5 and 4 pH units, wherein the pKa of the acid must be higher than the pKa of the base as explained above. In preferred embodiments, the $\Delta pKa$ is between 1.2 and 1.8, which is particularly useful for pH separation plateaus having a constant pH within the separation chamber of an FFE apparatus. In other preferred embodiments, the $\Delta pKa$ will be between about 2.5 and 3.3, the latter being particularly suitable for flat pH-gradients.

One characteristic of the A/B SBM is that the electrical conductivity of the medium is relatively low, although it will be appreciated that the conductivity must be sufficiently high to achieve acceptable separation of the analytes in a reasonable amount of time. Thus, the conductivity of the A/B SBM is typically between 50 and 1000 $\mu S/cm$, and more preferably between 50 and 500 $\mu S/cm$, although those of skill in the art will be aware that the exact conductivity in the separation medium will of course depend on the specifics of the separation/fractionation problem, the presence of other charged species in the medium (e.g., ions required for sample/analyte stability) and the electrochemical properties of the analyte.

Preferably, the A/B SBM comprise only one buffer acid and one buffer base. In other words, such separation media represent binary media wherein one acid function of a compound and one base function of the same or another compound essentially serve to establish a separation medium with the desired pH and conductivity profile. While good results may also be achieved with two or more buffer acids and buffer bases in the separation medium, it is typically advantageous to use as few components as possible, not only because it is easier to prepare and possibly cheaper to use, but also because the electrochemical properties of the medium will become more complex if the number of charged species present in the separation chamber is increased.

Suitable buffer bases in this context are, for example, taurine, glycine, 2-amino-butyric acid, glycylglycine, β-alanine, GABA, EACA, creatinine, pyridine-ethanol, pyridine-propanol, histidine, BISTRIS, morpholinoethanol, triethanolamine, TRIS, ammediol, benzylamine, diethylaminoethanol, trialkylamines, and the like. Suitable buffer acids are, for example, HIBA, acetic acid, picolinic acid, 4-pyridineethanesulfonic acid (PES), MES, ACES, MOPS, HEPES, EPPS, TAPS, AMPSO, CAPSO, α-alanine, GABA, EACA, 4-hydroxypyridine, 2-hydroxypyridine, and the like, provided the pKa relationships between the buffer acid and buffer base as described above is met.

Furthermore, binary buffer systems as disclosed in, e.g., U.S. Pat. No. 5,447,612 for separating analytes by FFE can also be employed. These binary media may be suitable for forming relatively flat pH gradients of between 0.4 to 1.25 pH units.

FFE Methods and Modes

A FFE method in accordance with embodiments of the present invention can be carried out using, e.g., one of the following operation methods.

Several FFE operation methods are known to those skilled in the art and are contemplated in the context of the present invention. For example, in certain embodiments of the present invention a sample can be separated according using a electrophoretic separation method selected from isoelectric focusing (IEF), zone electrophoresis (ZE), combinations thereof, or isotachophoresis (ITP)). The principles of these operation methods are, e.g., described in WO 2007/147862 and the co-pending provisional applications U.S. Ser. No. 60/945,246, U.S. Ser. No. 60/987,208, U.S. Ser. No. 60/885,792 U.S. Ser. No. 60/987,235 and U.S. Ser. No. 60/863,834, which are herewith incorporated by reference in their entirety.

Additionally, several FFE operation modes are known to those of skill in the art and are contemplated in the context of the present invention. For example, the sample and separation medium may be continuously driven towards the outlet end while applying an electrical field between the anode and the cathode of an FFE apparatus ("continuous mode"). Continuous mode in the context of FFE should be understood to mean that the injection step as well as the separation step occurs continuously and simultaneously. The electrophoretic separation occurs while the medium and the analytes pass through the electrophoresis chamber where the different species are being separated according to their pI (IEF), net charge density (ZE) or electrophoretic mobility (ITP). Continuous mode FFE allows continuous injection and recovery of the analytes without the need to carry out several independent "runs" (one run being understood as a sequence of sample injection, separation and subsequent collection and/or detection). It will be appreciated that continuous mode FFE includes separation techniques wherein the bulk flow rate is reduced (but not stopped) compared to the initial bulk flow rate while the analytes pass the separation space between the electrodes in order to increase the separation time. In the latter case, however, one can no longer speak of a true continuous mode because the reduction of the bulk flow rate will only make sense for a limited amount of a sample.

Another FFE operation mode known as the so-called "interval mode" or "static interval mode" in connection with FFE applications has also been described in the art. For example, a process of non-continuous (i.e. interval) deflection electrophoresis is shown in U.S. Pat. No. 6,328,868, the disclosure of which is hereby incorporated by reference. In this patent, the sample and separation medium are both introduced into an electrophoresis chamber, and then separated using an electrophoresis mode such as zone electrophoresis, isotachophoresis, or isoelectric focusing, and are finally expelled from the chamber through fractionation outlets. Embodiments of the '868 patent describe the separation media and sample movement to be unidirectional, traveling from the inlet end towards the outlet end of the chamber. This direction, unlike in traditional capillary electrophoresis, is shared by the orientation of the elongated electrodes. In the static interval mode described, e.g., in the '868 invention, acceleration of the sample between the electrodes caused by a pump or some other fluidic displacement element only takes place when the electrical field is off or at least when the voltage is ineffective for electrophoretic migration, i.e., when no part of the sample is being subjected to an effective electric field.

In other words, the interval process is characterized by a loading phase where the sample and media are introduced into the separation chamber of the electrophoresis apparatus, followed by a separation process where the bulk flow of the medium including the sample is halted while applying an electrical field to achieve separation. After separation/fractionation of the sample, the electrical field is turned off or reduced to be ineffective and the bulk flow is again turned on so that the fractionated sample is driven towards the outlet end and subsequently collected/detected in a suitable container, e.g., in a micro titer plate.

The so-called cyclic or cyclic interval mode in the context of FFE as used herein has been described in International application WO/2008/025806, hereby incorporated by reference in its entirety. In sum, the cyclic interval mode is characterized by at least one, and possible multiple reversals of the bulk flow direction while the sample is being held in the electrophoretic field between the elongated electrodes. In contrast to static interval mode, the sample is constantly in motion thereby allowing higher field strength and thus better (or faster) separation. Additionally, by reversing the bulk flow of the sample between the elongated electrodes, the residence time of the analytes in the electrical field can be increased considerably, thereby offering increased separation time and/or higher separation efficiency and better resolution. The reversal of the bulk flow into either direction parallel to the elongated electrodes (termed a cycle) can be repeated for as often as needed in the specific situation, although practical reasons and the desire to obtain a separation in a short time will typically limit the number of cycles carried out in this mode.

The terms "enzyme-linked immuno sorbent assay" or "ELISA" as used herein describe a biochemical technique used mainly in immunology to detect the presence of an antibody or an antigen in a sample. The ELISA has been used as a diagnostic tool in medicine and plant pathology, as well as a quality control check in various industries. The skilled person will know how to perform an ELISA.

Methods

In one aspect, the present invention relates to a method useful for diagnosis or prognosis of a pathologic condition characterized by the presence/absence of an endogenous hormone and/or hormone analog(s) thereof involved in diabetes or metabolic syndrome (analytes of interest) comprising:
  (a) quantitative separation of at least one of the hormone analog(s) and the endogenous hormone, or quantitative separation of at least two of the hormone analogs from a sample into a multiplicity of fractions and collection of at least those fractions comprising an endogenous hormone and/or hormone analog(s) thereof;
    with the proviso that if the common presence of the analog(s) and/or the endogenous hormone in the same fraction(s) interferes with measuring a parameter of one of said hormone analog(s) and/or said endogenous hormone by an analytical method employed in step (b), at least such hormone analog(s) and/or the endogenous hormone must be separated from each other in step (a);
  (b) measuring at least one parameter of the endogenous hormone or analog(s) thereof in one or more fraction(s) that comprise(s) the hormone and/or analog(s) of interest by an analytical method.

Certain preferred embodiments of this first aspect relate to a method for diagnosis or prognosis of a pathologic condition characterized by the presence/absence of an endogenous hormone and/or hormone analog(s) thereof involved in diabetes or metabolic syndrome (analytes of interest) comprising:
  (a) quantitative separation of at least one of the hormone analog(s) and the endogenous hormone, or quantitative separation of at least two of the hormone analogs from a sample into a multiplicity of fractions and collection of at least those fractions comprising an endogenous hormone and/or hormone analog(s) thereof;

with the proviso that if the common presence of the analog(s) and/or the endogenous hormone in the same fraction(s) interferes with measuring a parameter of one of said hormone analog(s) and/or said endogenous hormone by an analytical method employed in step (b), at least such hormone analog(s) and/or the endogenous hormone must be separated from each other in step (a);
(b) measuring at least one parameter of the endogenous hormone or analog(s) thereof in one or more fraction(s) that comprise(s) the hormone and/or analog(s) of interest by an analytical method;
(c) correlating the measured parameter of the endogenous hormone and/or the analog(s) with the presence, absence or severity of the pathologic condition.

Furthermore, a further aspect of the present invention relates to a method useful for diagnosis or prognosis of a pathologic condition characterized by the presence/absence of an endogenous hormone and/or hormone analog(s) thereof involved in diabetes or metabolic syndrome comprising:
(a) quantitative separation of at least one of the hormone analog(s) and the endogenous hormone, or quantitative separation of at least two of the hormone analogs from a sample into a multiplicity of fractions;
with the proviso that if the common presence of the analog(s) and/or the endogenous hormone in the same fraction(s) interferes with measuring a parameter of one of said hormone analog(s) and/or said endogenous hormone by an analytical method employed in step (b), at least such hormone analog(s) and/or the endogenous hormone must be separated from each other in step (a);
(b) online measuring at least one parameter of the endogenous hormone or analog(s) thereof in one or more fraction(s) that comprise(s) the hormone and/or analog(s) of interest by an analytical method not involving mass spectrometry.

Certain preferred embodiments of this second aspect relate to a method for diagnosis or prognosis of a pathologic condition characterized by the presence/absence of an endogenous hormone and/or hormone analog(s) thereof involved in diabetes or metabolic syndrome (analytes of interest) comprising:
(a) quantitative separation of at least one of the hormone analog(s) and the endogenous hormone, or quantitative separation of at least two of the hormone analogs from a sample into a multiplicity of fractions;
with the proviso that if the common presence of the analog(s) and/or the endogenous hormone in the same fraction(s) interferes with measuring a parameter of one of said hormone analog(s) and/or said endogenous hormone by an analytical method employed in step (b), at least such hormone analog(s) and/or the endogenous hormone must be separated from each other in step (a);
(b) online measuring at least one parameter of the endogenous hormone or analog(s) thereof in one or more fraction(s) that comprise(s) the hormone and/or analog(s) of interest by an analytical method except mass spectrometry;
(c) correlating the measured parameter of the endogenous hormone and/or the analog(s) with the presence, absence or severity of the pathologic condition.

Another aspect of the present invention relates to a method for determining the absence/presence of at least one hormone form of an endogenous hormone that is involved in diabetes or metabolic syndrome in a sample comprising:

(a) a liquid phase matrix free electrophoretic method for separating hormone form(s) whose common presence with the hormone form of interest in the same fraction(s) interfere with measuring a parameter of the hormone form of interest by an analytical method employed in step (b); and
(b) measuring at least one parameter of the hormone form of interest in one or more fraction(s) that are predicted to comprise the hormone form of interest by an analytical method.

In accordance with the principles of the underlying invention, preferred embodiments relate to methods wherein the separation of the analytes of interest, i.e., the endogenous hormone and/or hormone analog(s) thereof, is an electrophoretic separation, preferably a liquid phase matrix free separation such as a capillary electrophoretic separation or a free flow electrophoretic separation.

In the context of the present invention, the pI difference of the separated analytes of interest, i.e., the hormone analog(s) and/or the endogenous hormone, may be as low as 1.5 or even less, in fact it may in some instances be 1.0 or less, 0.4 or less, 0.2 or less, 0.1 or less, or 0.05 or less.

It will be understood that an electrophoretic separation can be carried out in several modes. Accordingly, certain preferred embodiments of the present invention relates to methods wherein the electrophoretic separation is carried out in an operation method selected from but not limited to the group consisting of zone electrophoresis, isoelectric focussing, combinations thereof, and isotachophoresis. The principles of these operation methods are, e.g., described in WO 2007/147862 and the co-pending provisional applications U.S. Ser. No. 60/945,246, U.S. Ser. No. 60/987,208, PCT/EP2008/050597, U.S. Ser. No. 60/987,235 and PCT/EP2007/061840.

In further preferred embodiments wherein the electrophoretic separation is FFE, the FFE is operated in continuous mode, interval mode or cyclic interval mode.

Certain preferred embodiments of this aspect of the invention relate to a method wherein the FFE separation method carried out as step (a) comprises:
1) forming within a free flow electrophoresis (FFE) chamber a separation zone between an anode and a cathode that comprises a zone I formed by at least one separation buffer medium type I and a zone II formed by at least one separation buffer medium type II,
wherein a separation buffer medium of type I comprises at least one additive at an effective concentration; and
wherein a separation buffer medium of type II does not contain the additive(s) at an effective concentration; and
2) introducing a sample into the separation zone; and
3) transferring at least one of the hormone analog(s) and/or the endogenous hormone from a separation medium type I into a separation medium type II or transferring at least one of the hormone analog(s) and/or the endogenous hormone from a separation medium type II into a separation medium type I during the free flow electrophoretic separation.

Further preferred embodiments relates to a method wherein the FFE separation method carried out as step (a) comprises:
1) forming within a free flow electrophoresis (FFE) chamber a separation zone between an anode and a cathode that comprises a zone I formed by at least one SBM type I that yields denaturing separation conditions and a zone II formed by at least one SBM type II that yields non-denaturing separation conditions; and
2) introducing a sample into the separation zone; and 3) transferring at least one of the hormone analog(s) and/or the endogenous hormone from a SBM type I into a SBM type II or transferring at least one of the hormone analog(s) and/or the endogenous hormone from a SBM type II into a SBM type I during the free flow electrophoretic separation.

In certain embodiments, the SBM type II yields native conditions, i.e., the non-denaturing conditions are native conditions.

Further preferred embodiments relate to methods wherein a FFE separation method is carried out as step (a), wherein at least one of the hormone analog(s) and/or the endogenous hormone is separated from an analyte that is an interaction partner of at least one of the hormone analog(s) and/or the endogenous hormone comprising:

introducing a sample comprising the hormone analog(s) and/or the endogenous hormone and the interaction partner thereof into a zone I;

wherein the presence of at least one additive at an effective concentration in zone I suppresses the interaction between the analyte and the interaction partner;

wherein the interaction partner remains in zone I, whereas the hormone analog(s) and/or the endogenous hormone is transferred into a zone II.

In certain embodiments, zone I of the latter FFE separation embodiment comprises or is a pH plateau.

In all embodiments that include a FFE separation method wherein more than one SBM type as used in the context of the present invention, preferred embodiments relate to methods wherein all analytes of interest (i.e., the hormone analog(s) and/or the endogenous hormone) are transferred from one SBM type into another SBM type.

In certain embodiments, the interaction partner of at least one analyte of interest is albumin, such as human albumin.

In methods wherein the separation of the analytes of interest is carried out by capillary electrophoresis or FFE, the SBM may comprise a buffer system selected from, but not limited to the group consisting of commercially available ampholytes, complementary multi pair buffer systems (CMPBS), volatile buffer systems, or binary buffer systems (NB media).

The skilled person will appreciate that in the context of the present invention, sample loss is preferably kept as low as possible. Sample loss may occur during sample preparation, during the separation of the analytes of interest and/or during buffer exchange steps between the separation step (a) and the analysis step (b) of a method contemplated herein.

Accordingly, preferred embodiments relate to methods that do not require an extensive sample preparation prior to the separation step comprised in a method according to embodiments of the present invention.

In accordance with certain preferred embodiments of the present invention, the preparation time of a sample such as blood, plasma, serum or urine prior to a separation step (a) takes less than 2 h, preferably less than 1 h, more preferably less than 0.5 h starting from the point of receiving the sample from an animal until the sample is subjected to the separation step as described herein.

Furthermore, preferred embodiments relate to methods wherein the sample loss during the separation is essentially zero. Thus, in preferred embodiments, an analyte of interest is essentially not retained by, e.g., solid materials of a separation device, i.e., the recovery rate of the analyte of interest is at least 95%, preferably at least 98%, more preferably at least 99% and most preferably at least 99.9%.

A third source of sample loss or loss of an unspecific amount of at least one analyte is a buffer exchange step subsequent to a separation method and prior to an analytical method comprised in the methods according to embodiments of the present invention.

Accordingly, it is preferred that the method does not require a buffer exchange step subsequent to the separation step (a) and prior to the analytical step (b).

Such a buffer exchange step can be avoided by choosing separation methods wherein the analyte of interest already elutes from the separation zone in a suitable buffer medium to perform a subsequent analytical method to measure a parameter of one analyte of interest, i.e., an analyte of interest elutes in a buffer from the separation zone that does not interfere with the subsequent analytical method.

This can be achieved by choosing either all separation media of a separation method compatible with a subsequent analysis method comprised in a method according to embodiments of the present invention, or by choosing a separation method employing different separation buffer medium types, wherein at least those fractions containing a separated analyte of interest are formed by a separation buffer medium (SBM) type II that whose components do not interfere with a subsequent analytical method. In the latter aspect, the analyte of interest is transferred during the separation method from a SBM type I that may be incompatible with the subsequent analytical method into the SBM type II. Such a separation and, optionally, transfer of an analyte of interest into a suitable medium is conveniently achieved by FFE.

Non-limiting examples for this aspect include FFE methods wherein the sample is introduced with or into a SBM type I exhibiting denaturing conditions and a separated analyte of interest is eluted in a SBM type II and subsequently analysed in an immuno assay requiring a buffer medium that exhibits native or non-denaturing conditions. Alternatively, the subsequent analytical method requires a buffer medium that does not absorb or emit radiation of a discrete wavelength, e.g., if the subsequent analytic method is Raman spectroscopy and a buffer type II does not adsorb or emit radiation in the measured range whereas a medium type I does adsorb or emit radiation in the measured range.

Further preferred embodiments relate to methods wherein a buffer exchange step is not required before the separation step, i.e., prior to step (a) of a method as described herein.

Further embodiments of the present invention relate to the separation of at least one analyte of interest, preferably all analytes of interest, from another compound that is not an analyte of interest. For example, such a situation may occur if it is desirable to separate an analyte(s) of interest from an abundant compound such as albumin.

Serum and plasma both contain high levels of proteins such as albumin that may obfuscate the detection of lower abundant compounds, such as analytes of interest according to the present invention. Assuming that the analytes of interest are not bound or complexed to one of those major proteins, the compound that is not an analyte of interest should be removed early in the process in order to reduce the complexity of the subsequent analysis in order to enhance the sensitivity of a subsequent analytical method such as mass spectrometry (MS).

The separation of analytes of interest from each other as well as the ability to collect the multiplicity of fractions subsequent to the separation method and prior to their analysis not only allows the application of subsequent analytical methods wherein the common presence of certain analytes of interest in a fraction would otherwise interfere with the measurement of a parameter of the analyte. Rather, the separation of the analytes of interest from each other and from further compounds that are present in a sample further offers the advantage of an enhanced sensitivity of the analysis. In other words, the methods in accordance with certain embodiments of the present invention are characterized by an enhanced selectivity and sensitivity compared to methods known in the prior art such as LC-MS/MS.

By separating the analytes of interest (e.g., by FFE or capillary electrophoresis), the biological background in the form of unspecific signals of immuno assays or drowning of signal(s) in mass spectrometry caused by the presence of abundant compounds is distinctly reduced. In contrast to the methods described herein, a LC-MS/MS-based analysis as used in the prior art requires extensive purification prior to the LC application to obtain detectable peaks in the subsequent MS/MS analysis. Such protocols to deplete abundant proteins are, e.g., disclosed in WO 2007/147862 which is incorporated herein by reference in its entirety.

Step (b) comprises the measurement of at least one parameter of an analyte of interest that is potentially present in a fraction. The skilled person will appreciate that the parameter to be measured depends on the analytical method, and will further understand how to decide which parameter is to be measured using a certain analytical method. For example, when the analytical method is a radio immuno assay, the parameter to be measured will be radioactive radiation emitted by the radio labelled detection reagent, or carrying out an ELISA, e.g., a sandwich ELISA, using a chemiluminescent reagent such as acridinium compounds linked to an insulin antibody, the measured parameter will be the emitted wave length. Further non-limiting examples of parameters to be measured, e.g., by SPR are the resonance angle, the resonance wavelength, the reflectance changes and the phase changes.

In certain preferred embodiments, the subsequent analytical method is selected from but not limited to the group consisting of immuno assay such as radio-immuno assay (RIA), memory lymphocyte immuno stimulation assay (MELISA), enzyme linked immuno sorbent assay (ELISA) or chemiluminescence assay, mass spectrometry, SPR, critical angle refractometry, total internal fluorescence (TIRF), total internal reflection phosphorescence, total internal reflection light scattering, evanescent wave elipsometry, Brewster angle reflectometry, circular dichroism, UV or UV-VIS-spectroscopy, IR-spectroscopy, pulsed amperometric detection, and Raman spectroscopy.

In preferred embodiments where the analysis is carried out online, the subsequent analytical method is selected from but not limited to the group consisting of SPR, critical angle refractometry, total internal fluorescence (TIRF), total internal reflection phosphorescence, total internal reflection light scattering, evanescent wave elipsometry, Brewster angle reflectometry, circular dichroism, UV or UV-VIS-spectroscopy, IR-spectroscopy, pulsed amperometric detection, and Raman spectroscopy.

Furthermore, certain embodiments of the present invention relate to methods wherein more than one parameter that correlates to one analyte of interest is measured by an analytical method. As non-limiting examples, surface plasmon resonance is suitable to measure more than one parameter such as resonance angle, resonance wavelength, reflectance changes, phase changes and any combination thereof. Alternatively, a first detection reagent of a subsequent immuno assay may comprise a radioisotope, i.e., the parameter is radioactivity, and a second detection reagent may be a chemiluminescent agent, i.e., the parameter is the emitted radiation.

The skilled person will appreciate that a standardized separation method employing standards of the analytes of interest will allow the determination of the elution pattern, i.e. it will be determined in which fraction a certain analyte of interest elutes from a separation zone. Thus, the presence/absence of an analyte of interest in a sample can be determined by measuring the predicted fractions regardless of whether or not the analyte is present in the examined fraction derived from the actual sample. In certain embodiments, it is contemplated that the first, the first two, the first three or the first four fractions adjacent on each side of the predicted fraction(s) are also measured for the presence/absence of the analyte of interest.

In preferred embodiments of the method aspects of the present invention, the analytical method is carried out to determine the concentration/amount of at least one analyte of interest present in a separated sample. In other preferred embodiments, the concentration/amount of all analytes of interest is determined. Alternatively, the concentration/amount ratio between the analytes of interest can be determined.

In further preferred embodiments, aspects of the invention relate to methods wherein in addition to the presence/absence, concentration/amount, or concentration/amount ratio of one endogenous hormone and/or analog(s), at least the absence/presence concentration/amount, or concentration/amount ratio of one further endogenous compound and/or analog(s) of the further endogenous compound is simultaneously measured by an analytical method. In other words, more than one endogenous compound and/or their corresponding analog(s) are simultaneously measured in such methods according to this aspect of the invention. The analytical method of step (b) is then used as a multiplexing analytical method. Non-limiting examples are multiplexing immuno arrays or SPR comprising a multiplexing biosensor.

In the preferred embodiments of this aspect, a further endogenous compound is selected from, but not limited to the group consisting of another hormone involved in diabetes or metabolic syndrome, an endogenous hormone that is not involved in diabetes and/or metabolic syndrome, a protein, a metabolite such as a metabolite of the glucose pathway, a nucleic acid.

Specific Analytical Methods

In embodiments wherein the analysis technique is an immuno assay, preferably ELISA, the measured parameter is selected from, but not limited to the group consisting of radioactivity, absorbed, scattered or emitted radiation such as UV, UV-VIS or near IR radiation. The absorbed, scattered or emitted radiation may be a result of chemiluminescence, fluorescence, phosphorescence, Raman-spectroscopy and the like. These methods are generally well-known in the art.

The chemiluminescence is typically caused by a chemical reaction such as the oxidation of chemiluminescent acridinium ester under alkaline conditions or enzymatic reaction such as the strepavidine-biotin peroxidase method. The enzymatic reactions or chemiluminescence, typically emitting visible or UV radiation having distinct wave length(s), can easily be detected and analysed by, e.g., UV-VIS-spectroscopy.

In preferred embodiments, the ELISA may be carried out as indirect ELISA, sandwich ELISA and competitive ELISA.

Methods that allow an online measurement are, e.g., SPR, critical angle refractometry, total internal fluorescence (TIRF), total internal reflection phosphorescence, total internal reflection light scattering, evanescent wave elipsometry, Brewster angle reflectometry, circular dichroism, UV-spectroscopy, IR-spectroscopy, pulsed amperometric detection, and Raman spectroscopy.

In other preferred embodiments, the separated analytes of interest (analog(s) and/or a endogenous hormone) are collected in a multiplicity of fractions, i.e., the fractions are collected subsequent to a separation step (a) and prior to an analysis technique of step (b).

The correlation of the measured parameter of the endogenous hormone and/or the analog(s) with the presence, absence or severity of the pathologic condition may provide a basis for an improved treatment and/or administration and/or dosage regime of one or more hormone analog(s) or for a balanced diet. Alternatively, the correlation is indicative of an abusive administration of the hormone or an analog thereof; or is indicative of doping.

Generally, the in vitro methods of the present invention allow or at least contribute to the diagnosis or prognosis of a specific pathological condition, or the methods may be indicative for the susceptibility of an animal to develop a pathological condition.

In preferred embodiments of the methods described herein, the endogenous hormone is insulin.

Assessment of insulin analogs in the plasma of diabetic patients is a sophisticated diagnostic problem, especially if different analogs are applied concomitantly or if endogenous insulin is also present. Non-limiting examples for insulin analogs are heterologous insulin, Glargine, Lispro, Aspart, Glulisine and Detemir.

The term "heterologous" insulin as used herein refers to insulin analogs produced by animals of a different species (e.g., endogenous is human insulin and heterologous insulin is pig or albumin insulin), or insulin analogs produced by a different animal of the same species, with the proviso that the amino acid sequence of the heterologous insulin differs from the endogenous insulin by at least 1 amino acid (e.g., by mutation, deletion or addition), and/or the heterologous differs from the endogenous insulin by a modification of at least one amino acid. As will be apparent, the same definition of a heterologous analog also applies to other endogenous hormones such as GLP-1 and the like.

Glargine, Lispro, Aspart, Glulisine and Detemir are well-known insulin analogs and are commercially available under different trade names. The amino acid sequences and/or modifications of these analogs compared to human insulin are summarized in Table 1:

more than one insulin form, except for insulin Lispro via a specific antibody, or via MS techniques that are time consuming and need excessive sample preparation prior to the analysis.

In contrast, the method according to the present invention allows to employ analytical methods that are normally not useful for determining/measuring a parameter of one analyte of interest as long as the analytes of interest are not quantitatively separated, i.e. the common presence of more than one insulin form leads to a cross reaction or interference with the analytical method. For example, merely one specific immunoassay is commercially available for insulin Lispro and all other analogs show cross-reactivity with different assays for regular human insulin. Accordingly, all insulin analogs listed above except Lispro, i.e. Aspart, Glulisine, Detemir and Glargine, have to be quantitatively separated from endogenous human insulin and/or from each other to allow an evaluation and/or quantification of the different forms in a sample by, e.g., ELISA. In other words, following the principles of the present invention, certain embodiments relate to a method wherein any of the analogs and/or the endogenous insulin are separated from each other, with the proviso that insulin Lispro and endogenous insulin can be present in the same fraction(s) of the separation step since each of the two forms can be quantified in the presence of the other form (using, e.g., ELISA with the Lispro specific antibody followed by an Elisa using a cross-reactive antibody).

It will be understood that these principles also apply to any other hormone involved in diabetes or metabolic syndrome, such as GLP-1.

Certain embodiments of the present invention relate to methods wherein a sample comprises at least one hormone analog and the endogenous hormone.

Further embodiments of the present invention relate to methods wherein a sample comprises at least 2, 3, 4 or 5 hormone analogs, and, in each case, optionally further comprising the endogenous hormone.

Additional preferred embodiments relate to methods wherein at least 3 analytes of interest are quantitatively separated from each other in step (a), or wherein all analogs of an endogenous hormone are quantitatively separated from each

TABLE 1

Sequences and pl's of human insulin and analogs thereof.
Differences in the amino acid sequence are underlined.

| Product | Sequence | IEP |
|---|---|---|
| insulin (endogenous) | a-Chain GIVEQCCTSICSLYQLENYCN (SEQ ID NO: 1)<br>b-Chain FVNQHLCGSHLVEALYLVCGERGFFYTPKT (SEQ ID NO: 2) | 6.0 |
| Glargine (Sanofi-Aventis) | a-Chain GIVEQCCTSICSLYQLENYCG (SEQ ID NO: 3)<br>b-Chain FVNQHLCGSHLVEALYLVCGERGFFYTPKTRR (SEQ ID NO: 4) | 7.2 |
| Lispro (Lilly) | a-Chain GIVEQCCTSICSLYQLENYCN (SEQ ID NO: 5)<br>b-Chain FVNQHLCGSHLVEALYLVCGERGFFYTKPT (SEQ ID NO: 6) | 6.0 |
| Aspart (Novo Nordisk) | a-Chain GIVEQCCTSICSLYQLENYCN (SEQ ID NO: 7)<br>b-Chain FVNQHLCGSHLVEALYLVCGERGFFYTDKT (SEQ ID NO: 8) | 5.1 |
| Glulisine (Sanofi-Aventis) | a-Chain GIVEQCCTSICSLYQLENYCN (SEQ ID NO: 9)<br>b-Chain FVKQHLCGSHLVEALYLVCGERGFFYTPET (SEQ ID NO: 10) | 5.3 |
| Detemir (Novo Nordisk) | a-Chain GIVEQCCTSICSLYQLENYCN (SEQ ID NO: 1q)<br>b-Chain FVNQHLCGSHLVEALYLVCGERGFFYTPK-$NH_2$-$CO(CH_2)_{12}$-$CH_3$ (SEQ ID NO: 12) | 6.0 |

To the best of the applicants knowledge, the presence and/or concentration and/or amount of specific forms of insulin cannot be determined in a sample (or fraction) comprising other, or wherein all hormone analog(s) and the endogenous hormone are quantitatively separated from each other in step (a).

Further preferred embodiments relate to methods wherein each fraction containing an endogenous hormone does not contain an analog thereof, or wherein each fraction containing an analog does not contain another analog of the endogenous hormone, or wherein one or more fractions do not contain the endogenous hormone or analog(s) thereof, and/or wherein the endogenous hormone is absent in a sample.

Preferably, an analytical method carried out in step (b) of the methods described herein does not alter the primary structure of the analytes of interest, i.e., the primary structure of an analyte of interest is not destroyed, or ionised by electron bombardment or laser light, which is for example the case in mass spectrometry (MS).

Kits

Another aspect of the present invention relates to kits useful for performing the methods according to the present invention.

A kit according to the present invention comprises a standard of the endogenous hormone and/or analogs thereof as defined herein and buffer components for the preparation of the separation buffer medium (a) to perform step (a) and, optionally, components to prepare the analytical buffer(s) to perform step (b). It will be understood that the components may be delivered separately or as at least one solid or liquid mixture.

In embodiments wherein the separation method is a matrix free electrophoretic separation such as capillary electrophoresis or FFE, the skilled person will understand that only one SBM (e.g. in ZE) or, depending on the desired method (e.g. IEF), more than one SBM can be provided for the electrophoretic separation. For example, in IEF more than one SBM may be delivered to prepare a linear gradient. Therefore, the number of different SBM and, optionally, the number of different SBM types can also be between 2 and 15, preferably between 3 and 12, and more preferably between 3 and 7. In embodiments wherein more than one buffer type is used, at least one of the SBMs is a SBM type I as defined herein. The skilled person will appreciate that also other numbers of SBM such as up to 20, 30 or 40 are possible. In the context of FFE, it is noted that the SBM may also have utility as a stabilizing and/or focus medium.

Certain preferred embodiments of the present invention relate to methods wherein at least one separation buffer comprising a separated analyte of interest is suitable to act as an analytical buffer in a subsequent analysis method.

The SBM contemplated herein may be selected, prepared and used alone or, alternatively, together with other stabilizing media, focus media and SBMs, respectively.

Preferably, the kit provided herein is for carrying out a FFE method according to embodiments of the present invention. In such embodiments, the kit comprises at least the buffer compounds for the buffer system and at least one additive for the preparation of an SBM type I and at least one SBM type II.

Since anodic and cathodic stabilization are both particularly useful for successful electrophoretic applications, particularly in FFE, the kit will in addition to the SBM preferably comprise one anodic and/or one cathodic stabilizing medium as defined herein. The stabilizing medium may be a cathodic stabilizing medium and/or an anodic stabilizing medium. They are generally located between the anode (and/or cathode, respectively) and further SBM in the separation zone.

The kit may comprise at least one, several or all SBMs and, optionally, SBM types (type I and/or type II) as aqueous solutions that are ready to be used in FFE applications according to the present invention (i.e., all components are present in the desired concentration for the electrophoretic separation problem), or it may contain one, several or all of the SBMs and, optionally, SBM types in the form of a concentrated aqueous stock solution that is to be diluted with a pre-determined amount of solvent to the appropriate concentration prior to their use. Alternatively, the kit may comprise one, several or all component of the kit in dry form or lyophilized form, wherein the components are to be dissolved with a predetermined amount of solvent, e.g. water or the buffer system in water, prior to its use in an electrophoretic separation process.

It will be understood that each component such as each dried component and/or each stock solution and/or each solution ready for use may each be separately placed in a sealed container, or combined as appropriate.

It will be further understood that in embodiments involving FFE, all of the preferred SBMs described herein, as well as the preferred cathodic and/or anodic stabilizing media, may be included in the kits of the present invention.

It is generally preferred that each medium (SBM, cathodic stabilizing medium, anodic stabilizing medium, counter flow medium) will be present in a separate container, although it will be apparent to those of skill in the art that other combinations and packaging options may be possible and useful in certain situations. For example, the separation media for IEF applications may consist of a distinct number of "sub-fractions" having different concentrations of the ingredients (and thereby a different pH) in order to create a pre-formed pH gradient within the electrophoresis apparatus. In one embodiment, the pH of each SBM used to form the gradient is different. The number of sub-fractions employed in IEF applications will depend on the separation problem, the desired pH span achieved with the SBM and the electrophoresis apparatus used for the separation. In FFE applications, the apparatus will typically comprise several media inlets (e.g., N=7, 8 or 9 inlets), so that the sub-media creating the separation space within the apparatus may be introduced into at least one to a maximum of N-2 inlets (at least one inlet on each side is usually reserved for a stabilizing medium, if present). The number of SBMs, which can be inserted into an apparatus suitable for FFE, is thus typically between 2 and 15, or between 3 and 12, or between 4 and 9.

In particularly preferred embodiments, the separation media in the kit will be formed by binary buffer systems, comprising only one buffer acid and one buffer base. It is contemplated that all of the separation media described herein, be they preferred or not, may be included in the kits of the present invention.

In further preferred embodiments, a kit according to the present invention further comprises at least one product manual that describes one or more experimental protocols to carry out a method according to the present invention, and optionally storage conditions for the components. An experimental protocol may comprise a protocol to carry out a separation method according to step (a), wherein the separation method is preferably capillary electrophoresis or free flow electrophoresis, an analytical protocol to carry out an analytical method according to step (b) and, optionally, guidelines to carry out step (c).

Apparatus

A further aspect of the present invention relates to an apparatus for carrying out an FFE method as part of an in vitro method described herein.

Such an FFE apparatus for carrying out a method according to embodiments of the present invention may comprises:

an electrophoresis chamber comprising a set of electrodes, wherein at least one of the electrodes is a cathode and at least one of the electrodes is an anode, and a separation zone interposed therebetween, wherein the apparatus further contains means for introducing SBM's into the separation zone; and optionally, means for forming stabilizing media within the separation zone; and fraction outlets that transfer the fractions into a suitable container to perform a subsequent analytical method according to step (b), or, optionally, fraction outlets that are combined with a subsequent online analytical device.

In further preferred embodiments, the means of the FFE apparatus are subdivided into means for forming a zone I formed by at least one SBM type I and means for forming a zone II formed by at least one SBM type II.

In other embodiments, such an FFE apparatus for carrying out step (a) of a method according to embodiments of the present invention comprises:

an electrophoresis chamber comprising a set of electrodes, wherein at least one of the electrodes is a cathode and at least one of the electrodes is an anode, and a separation zone interposed therebetween;

a multiplicity of separation buffer media inlets in fluidic connection with the separation zone;

optionally a sample inlet capable of fluid communication with the separation zone;

fraction outlets that transfer the fractions into a suitable container to perform a subsequent analytical method, or, optionally, fraction outlets that are combined with a subsequent online analytical device.

In certain embodiments, the apparatus of this aspect of the invention further comprises a zone I formed by at least one SBM type I and a zone II formed by at least one SBM type II.

In certain preferred embodiments, the subsequent online analytical device is an SPR device having a multiplicity of flow channels or a Raman-spectroscopy device. The skilled person will understand that all fractions, only the fraction(s) wherein an analyte of interest in a sample is predicted to elute, or the fraction(s) wherein an analyte of interest is predicted to elute and additionally the first, the first two, the first three or the first four fractions that are adjacent on each side of the predicted fraction(s) are connected with the subsequent online analysis device.

Accordingly, the use of an apparatus as defined above in performing a separation of analytes of interest from each other by free flow electrophoresis comprised in a method according to the present invention is also an embodiment of the present invention.

It will be apparent to those of skill in the art that many modifications and variations of the embodiments described herein are possible without departing from the spirit and scope of the present invention. The present invention and its advantages are further illustrated in the following, non-limiting examples.

EXAMPLES

Example 1

Separation of Insulin Detemir and Albumin Under Denaturing Conditions (in SBM Type I) and Elution of Insulin Detemir Under Native Conditions (in SBM Type II)

insulin Detemir is a long-acting human insulin analogue for maintaining the basal level of insulin. It is an insulin analogue in which to the lysine amino acid at position B29 a fatty acid (myristic acid) is bound. It strongly interacts under native conditions with albumin through the fatty acid at position B29.

The separation medium and stabilizing media were tested on a BD™ Free Flow Electrophoresis System in FF-IEF mode using a quality control solution. The apparatus was set up comprising seven media inlets (E1-E7) and four sample inlets (S1-S4). Anodic stabilizing medium was introduced into inlet E1. The cathodic stabilizing medium was introduced into inlet E7 and the sample was introduced via sample inlet S4. The total time of electrophoresis was approximately 10 minutes. The voltage applied was 1200V and the current was 37 mA. The sample and the media were introduced at a flow rate of 1.5 ml/h and 120 ml/h, respectively.

After the test of the separation medium and stabilizing media, an insulin Detemir standard was run to evaluate fractions comprising the analyte of interest.

Subsequently, insulin Detemir was spiked into a blood plasma sample and the sample was run under the same separation conditions.

All samples were introduced into a zone I (E4) yielding denaturing conditions that suppresses insulin Detemir-albumin interaction. Insulin Detemir was eluted in fractions containing SBM type II yielding non-denaturing conditions.

Anodic stabilizing medium: 100 mM $H_2SO_4$ 50 mM HAc 200 mM 2-Ami.Butt. 30 mM Glycylglycin (pH=2.16; conductivity: 5650 µS/cm) (E1);

Cathodic stabilizing medium: 150 mM NaOH 300 mM β-Alanin 30 mM ethanolamine (pH=10.09; conductivity: 3200 µS/cm) (E9);

Separation Medium:

| | Media Inlet | | | |
|---|---|---|---|---|
| | E2 | E3 | E4 | E5  E6 |
| Media | 7.5% Prolyte1 17.5% Prolyte2 diluted ⅓ with 50 mM HAc | | 40 mM MOPS X mM GABA + 0.3% HPMC 8M Urea | 20% Prolyte2 |
| pH | 5.62 | | 6.07 | 7.14 |
| Conductivity (µS/cm) | 477 | | 359 | 343 |

The pH of each of the FFE fractions was determined using a pH electrode and is presented by the graph in FIG. 2. Colored pI-markers were separated to evaluate the separation performance of the system. In addition, the absorbance of the fraction at λ=420 nm, 515 nm, and 595 nm which represent the absorbance of the respective pI-markers are reported in FIG. 2.

The insulin Detemir standard eluted into fractions 42 to 45 (see FIG. 3).

FIG. 4 depicts a silver stained gel showing the successful separation of insulin Detemir from albumin. Insulin Detemir eluted into fractions of SBM type II (yielding non-denaturing conditions), whereas albumin retained in fractions formed by SBM's of type I (yielding denaturing conditions).

Example 2

Separation of Insulin and/or Insulin Analogs from Each Other Using FFE-IEF

The separation medium and stabilizing media were tested on a BD™ Free Flow Electrophoresis System in FF-IEF mode using a quality control solution. The apparatus was set up comprising seven media inlets (E1-E7) and four sample inlets (S1-S4). Anodic stabilizing medium was introduced into inlets E1 and E2. The cathodic stabilizing medium was introduced into inlets E6 and E7. Samples were introduced via sample inlet S4. The voltage applied was 400V and the current was 25 mA. The sample and the media were introduced at a flow rate of 1.5 ml/h and 120 ml/h, respectively.

The following samples were separated: Serum only, 50 mU/l Glargine and 50 mU/l human insulin spiked in serum, 50 mU/l Glulisine and 50 mU/l Glargine spiked in serum, 50 mU/l Glulisine and 50 mU/l human insulin spiked in serum.

Anodic stabilizing medium: 100 mM $H_2SO_4$ (pH=1.02; conductivity: 39100 µS/cm) (E1 and E2);

Cathodic stabilizing medium: 150 mM NaOH 50 mM ethanol amine (pH=12.67; conductivity: 29500 µS/cm) (E6 and E7);

Separation Medium:

|  | Media Inlet | | |
| --- | --- | --- | --- |
|  | E3 | E4 | E5 |
| Media | 14.3% Prolyte1 | 30 mM MES 100 mM Glygly 14% Prolyte 2 | 25% Prolyte 2 |
| pH | 5.62 | 6.07 | 7.14 |
| Conductivity (µS/cm) | 477 | 359 | 343 |

The pH of the FFE fractions of the human serum sample comprising no human insulin or analogs thereof was determined using a pH electrode and is presented by the graph in FIG. 5. Colored pI-markers were separated to evaluate the separation performance of the system. In addition, the absorbance of the fraction at λ=420 nm, 515 nm, and 595 nm which represent the absorbance of the respective pI-markers are reported in FIG. 5.

FIG. 6 shows the corresponding silver stained SDS-PAGE gel obtained for the various fractions demonstrating the elution profile of the sample without insulin or analog(s) thereof.

FIG. 7 shows the corresponding silver stained SDS-PAGE gel obtained for the various fractions of the separation of Glargine and human insulin spiked in human serum. The gel indicates the quantitative separation of insulin Glargine which elutes in fractions 62 and 63 from human insulin which elutes in fractions 57 to 59.

FIG. 8 shows the corresponding silver stained SDS-PAGE gel obtained for the various fractions of the separation of Glargine and Glulisine spiked in human serum. The gel indicates the quantitative separation of insulin Glargine which elutes in fractions 62 and 63 from Glulisine which elutes in fractions 51 to 52.

FIG. 9 shows the corresponding silver stained SDS-PAGE gel obtained for the various fractions of the separation of Glulisine and human insulin spiked in human serum. The gel indicates the quantitative separation of insulin Glulisine which elutes in fractions 51 and 52 from human insulin which elutes from fractions 57 and 58.

The invention claimed is:

1. A method for determining the presence of at least one hormone form of an endogenous hormone that is involved in diabetes or metabolic syndrome in a sample comprising:
   (a) forming within a free flow electrophoretic (FFE) chamber a separation zone between an anode and a cathode that comprises a zone I formed by at least one separation buffer medium type I (SBM type I) and a zone II formed by at least one separation buffer medium type II (SBM type II),
   wherein the SBM type I yields denaturing conditions and comprises at least one additive at an effective concentration and the SBM type II yields non-denaturing conditions and does not contain the additive at the effective concentration;
   (b) introducing the sample into the separation zone; and
   (c) transferring the at least one hormone form from the SBM type I into the SBM type II, or transferring the at least one hormone form from the SBM type II into the SBM type I during the FFE separation, thereby separating the hormone form from an interfering form that would interfere with measuring a parameter of the hormone form by an analytical method employed in step (d), wherein the endogenous hormone is selected from the group consisting of insulin, glucagon-like-peptide 1 (GLP-1), ghrelin, cholecystokinin (CKK), leptin, and obestatin; and (d) measuring the parameter of the hormone form by the analytical method.

2. The method according to claim 1, wherein the electrophoretic separation of step (c) is carried out in an operation method selected from the group consisting of zone electrophoresis, isoelectric focusing, combinations thereof, and isotachophoresis.

3. The method according to claim 1, wherein the sample comprises a second hormone form, and wherein the at least one hormone form and the second hormone form are quantitatively separated from each other.

4. The method according to claim 1, wherein the hormone form is involved in diabetes type I or diabetes type II.

5. The method according to claim 1, wherein the endogenous hormone is insulin, and wherein the at least one hormone form is selected from the group consisting of heterologous insulin, Glargine, Lispro, Aspart, Glulisine, and Detemir.

6. The method according to claim 1 wherein the analytical method in step (b) step (d) is selected from the group consisting of immuno assay, mass spectrometry, SPR, critical angle refractometry, total internal fluorescence (TIRF), total internal reflection phosphorescence, total internal reflection light scattering, evanescent wave elipsometry, Brewster angle reflectometry, circular dichroism, UV or UV-VIS-spectroscopy, IR-spectroscopy, pulsed amperometric detection, and Raman spectroscopy.

7. The method according to claim 1 wherein the analytical method in step (d) comprises online measuring of the parameter measured in step (d) and is selected from the group consisting of SPR, critical angle refractometry, total internal fluorescence (TIRF), total internal reflection phosphorescence, total internal reflection light scattering, evanescent wave elipsometry, Brewster angle reflectometry, circular dichroism, UV or UV-VIS-spectroscopy, IR-spectroscopy, pulsed amperometric detection, and Raman spectroscopy.

8. The method according to claim 1, wherein the parameter correlates with the presence/absence, amount, concentration, weight ratio, or concentration ratio of the at least one hormone form.

9. The method according to claim 1, wherein the analytical method is carried out to determine the concentration/amount of the at least one hormone form that is present in the sample, and wherein the concentration/amount of the at least one hormone form that is present in the sample is determined, wherein the method further comprises:

determining the absence/presence of a second hormone form of the endogenous compound comprising simultaneously measuring by the analytical method the second hormone form, wherein the second hormone form is selected from the group consisting of another hormone involved in diabetes or metabolic syndrome, a hormone that is not involved in diabetes and metabolic syndrome, a protein, a saccharide, a nucleic acid, and a metabolite of the glucose pathway.

10. The method according to claim 1, wherein the analytical method is a multiplexing immuno array or SPR comprising a multiplexing biosensor.

11. The method according to claim 1, wherein the at least one hormone form is separated from an interaction partner of the at least one hormone form, wherein the introduction step comprises introducing the sample comprising the hormone form and the interaction partner into the zone I, wherein the presence of the at least one additive at the effective concentration in the zone I suppresses an interaction between the hormone form and the interaction partner, wherein the interaction partner remains in the zone I, whereas the hormone form is transferred into the zone II, wherein the zone I comprises a pH plateau, wherein the interaction partner is albumin, and wherein the endogenous hormone is a peptide hormone.

12. The method according to claim 3, wherein the at least one hormone form has an amino acid sequence that differs from an amino acid sequence of another analog of the endogenous hormone by at most 5 amino acids, wherein the at least one hormone form differs from the other analog by a modification of at least one amino acid, and wherein the modification comprises a substituent covalently attached to the at least one amino acid that is selected from the group consisting of a $C_1$-$C_{20}$ fatty acid, a $C_1$-$C_{20}$ alkyl, a $C_1$-$C_{20}$ alkanoyl, a monosaccharide, a disaccharide, a trisaccharide, a polysaccharide, a phosphate, a sulfonate, and a sialyl residue.

* * * * *